US012384707B2

(12) United States Patent
Gupta et al.

(10) Patent No.: US 12,384,707 B2
(45) Date of Patent: Aug. 12, 2025

(54) SYSTEM AND METHOD FOR TREATMENT OF ANIMAL MANURE CONTAINING WASTEWATER

(71) Applicant: Evoqua Water Technologies Canada Ltd, Fredericton (CA)

(72) Inventors: Hari B. Gupta, Schaumburg, IL (US);
James M. Ceklosky, Canonsburg, PA (US); Ivan Zhu, Cranberry, PA (US);
David Berger, Wampum, PA (US);
Daniel B. Scott, Fredericton (CA);
Frank Sassaman, Fombell, PA (US);
William Kohl, Madison, WI (US);
Shannon Grant, New Maryland (CA);
Mark Hunsaker, Elk Grove Village, IL (US)

(73) Assignees: Evoqua Water Technologies LLC, Pittsburgh, PA (US); Evoqua Water Technologies Canada Ltd., Fredericton (CA)

( * ) Notice: Subject to any disclaimer, the term of this patent is extended or adjusted under 35 U.S.C. 154(b) by 415 days.

(21) Appl. No.: 17/802,944

(22) PCT Filed: Feb. 26, 2021

(86) PCT No.: PCT/US2021/019882
§ 371 (c)(1),
(2) Date: Aug. 27, 2022

(87) PCT Pub. No.: WO2021/173978
PCT Pub. Date: Sep. 2, 2021

(65) Prior Publication Data
US 2023/0348305 A1    Nov. 2, 2023

Related U.S. Application Data

(60) Provisional application No. 62/982,899, filed on Feb. 28, 2020, provisional application No. 62/984,376, (Continued)

(51) Int. Cl.
*C02F 3/28* (2023.01)
*C02F 1/44* (2023.01)
(Continued)

(52) U.S. Cl.
CPC ............ *C02F 3/2826* (2013.01); *C02F 3/286* (2013.01); *C02F 3/2893* (2013.01); *C02F 9/00* (2013.01);
(Continued)

(58) Field of Classification Search
CPC ...... C02F 3/2826; C02F 3/286; C02F 3/2893; C02F 9/00; C02F 1/441; C02F 1/442;
(Continued)

(56) References Cited

U.S. PATENT DOCUMENTS 10,737,958 B2   8/2020   Church et al.
2004/0025715 A1  2/2004   Bonde et al.
(Continued)

FOREIGN PATENT DOCUMENTS

| DE | 102004030482 A1 | 8/2005 | |
|----|----|----|----|
| EP | 3517505 A1 | 7/2019 | |
| JP | 6649273 B2 * | 2/2020 | ............ C02F 1/4693 |

OTHER PUBLICATIONS

Machine-generated English translation of JP 6649273, generated on Dec. 9, 2024.*
(Continued)

*Primary Examiner* — Fred Prince

(57) ABSTRACT

Methods of treating animal organic material are disclosed herein. The methods include diluting the animal organic
(Continued)

material to produce an organic material slurry, anaerobically digesting the organic material slurry to produce a biogas and a digestate, separating the digestate to produce a digestate solids and a filtrate, removing ammonia from the filtrate, removing organic contaminants and divalent anions from the filtrate, concentrating the filtrate to produce a retentate and a permeate, combining the digestate solids and the retentate to produce a solids product, and returning the permeate to dilute the animal organic material. Systems for treatment of animal organic material are also disclosed herein. The systems include a dilution tank, an anaerobic digester, a first solids-liquid separation subsystem, an ammonia-reducing column, a second solids-liquid separation subsystem, a production water storage tank, and a solids product tank.

26 Claims, 5 Drawing Sheets

Related U.S. Application Data filed on Mar. 3, 2020, provisional application No. 63/007,655, filed on Apr. 9, 2020, provisional application No. 63/026,405, filed on May 18, 2020, provisional application No. 63/050,329, filed on Jul. 10, 2020, provisional application No. 63/082,748, filed on Sep. 24, 2020.

(51) Int. Cl.

| | | |
|---|---|---|
| *C02F 1/66* | (2023.01) | |
| *C02F 5/06* | (2023.01) | |
| *C02F 9/00* | (2023.01) | |
| *C02F 11/04* | (2006.01) | |
| *C02F 11/12* | (2019.01) | |
| *C02F 11/14* | (2019.01) | |
| *C05F 3/00* | (2006.01) | |
| *C05F 17/10* | (2020.01) | |
| *C12M 1/00* | (2006.01) | |
| *C12M 1/107* | (2006.01) | |
| C02F 11/127 | (2019.01) | |
| C02F 11/143 | (2019.01) | |
| C02F 11/147 | (2019.01) | |
| C02F 101/16 | (2006.01) | |
| C02F 101/30 | (2006.01) | |
| C02F 103/20 | (2006.01) | |

(52) U.S. Cl.
CPC ............. *C05F 17/10* (2020.01); *C12M 21/04* (2013.01); *C12M 45/03* (2013.01); *C02F 1/441* (2013.01); *C02F 1/442* (2013.01); *C02F 1/444* (2013.01); *C02F 1/66* (2013.01); *C02F 5/06* (2013.01); *C02F 11/04* (2013.01); *C02F 11/127* (2013.01); *C02F 11/143* (2019.01); *C02F 11/147* (2019.01); *C02F 2101/16* (2013.01); *C02F 2101/30* (2013.01); *C02F 2103/20* (2013.01); *C02F 2203/004* (2013.01); *C02F 2209/02* (2013.01); *C02F 2209/06* (2013.01); *C02F 2209/07* (2013.01); *C02F 2209/08* (2013.01); *C02F 2209/10* (2013.01); *C02F 2209/14* (2013.01); *C02F 2303/02* (2013.01); *C02F 2303/24* (2013.01); *C02F 2305/06* (2013.01); *C05F 3/00* (2013.01); *Y02A 40/20* (2018.01); *Y02E 50/30* (2013.01); *Y02P 20/133* (2015.11); *Y02P 20/145* (2015.11); *Y02W 30/40* (2015.05)

(58) Field of Classification Search
CPC .... C02F 1/444; C02F 1/66; C02F 5/06; C02F 11/04; C02F 11/127; C02F 11/143; C02F 11/147; C02F 2101/16; C02F 2101/30; C02F 2103/20; C02F 2203/004; C02F 2209/02; C02F 2209/06; C02F 2209/07; C02F 2209/08; C02F 2209/10; C02F 2209/14; C02F 2303/02; C02F 2303/24; C02F 2305/06; C05F 17/10; C05F 3/00; C12M 21/04; C12M 45/03; Y02A 40/20; Y02E 50/30; Y02P 20/133; Y02P 20/145; Y02W 30/40
USPC ........ 210/603, 631, 252, 259, 260, 903, 908
See application file for complete search history.

(56) References Cited

U.S. PATENT DOCUMENTS

| | | | |
|---|---|---|---|
| 2004/0164021 | A1 | 8/2004 | Li et al. |
| 2006/0096163 | A1* | 5/2006 | Dickinson ................. C10L 5/46 |
| | | | 44/552 |
| 2014/0199743 | A1 | 7/2014 | Hughes et al. |
| 2015/0329399 | A1 | 11/2015 | Kumar et al. |
| 2016/0176768 | A1 | 6/2016 | Norddahl et al. |
| 2020/0157739 | A1* | 5/2020 | Toll .................... D21C 11/0007 |

OTHER PUBLICATIONS

International Search Report, corresponding PCT/US2021/19882, dated May 19, 2021.
Fiocchi, Nicola, "Extended European Search Report", European Patent Application No. 21761690.3, mailed Nov. 24, 2023, 9 pages.
Gienau, T. et al., "Nutrient recovery from anaerobic sludge by membrane filtration: pilot tests at a 2.5 MW biogas plant", International Journal of Recycling of Organic Waste in Griculture, Biomed Central Ltd, London, Uk, vol. 7, No. 4, Sep. 5, 2018, pp. 325-334, XP021262209, ISSN: 2195-3228, DOI: 10.1007/S40093-018-0218-6.
McOrmond, Alex, Requisition by the Examiner, Canadian Patent Application No. 3,169,138, mailed Oct. 27, 2023, 6 pages.

\* cited by examiner

SYSTEM AND METHOD FOR TREATMENT OF ANIMAL MANURE CONTAINING WASTEWATER

CROSS-REFERENCE TO RELATED APPLICATIONS

This application claims priority under 35 U.S.C. § 119(e) to U.S. Provisional Application Ser. No. 62/982,899, titled "System and Method for the Treatment of Animal Manure Containing Wastewater" filed Feb. 28, 2020, U.S. Provisional Application Ser. No. 62/984,376, titled "System and Method for the Treatment of Animal Manure Containing Wastewater" filed Mar. 3, 2020, U.S. Provisional Application Ser. No. 63/026,405, titled "System and Method for the Treatment of Animal Manure Containing Wastewater" filed May 18, 2020, U.S. Provisional Application Ser. No. 63/050,329, titled "System and Method for the Treatment of Animal Manure Containing Wastewater" filed Jul. 10, 2020, U.S. Provisional Application Ser. No. 63/082,748, titled "System and Method for the Treatment of Animal Manure Containing Wastewater" filed Sep. 24, 2020, and U.S. Provisional Application Ser. No. 63/007,655, titled "Anaerobic Digester System and Method" filed Apr. 9, 2020, each of which is incorporated herein by reference in its entirety for all purposes.

FIELD OF TECHNOLOGY

Aspects and embodiments disclosed herein are generally related to treatment of animal manure containing wastewater, and more specifically, to recovery of water during treatment of animal manure containing wastewater.

SUMMARY

In accordance with one aspect, there is provided a method of treating animal organic material comprising solids. The method may comprise diluting the animal organic material to produce an organic material slurry. The method may comprise anaerobically digesting the organic material slurry to produce a biogas and a digestate comprising ammonia. The method may comprise separating the digestate to produce a digestate solids and a filtrate. The filtrate may have less than 1 ppm total suspended solids (TSS). The method may comprise removing ammonia from the filtrate to produce an ammonia-depleted filtrate. The method may comprise removing organic contaminants and divalent anions from the ammonia-depleted filtrate to produce an organic containing reject and an organic-depleted filtrate. The method may comprise concentrating the organic-depleted filtrate to produce a concentrated retentate and a return permeate. The method may comprise combining the digestate solids, the organic containing reject, and the concentrated retentate to produce a solids product. The method may comprise directing the return permeate to dilute the animal organic material.

In some embodiments, the return permeate may have 200-500 ppm total dissolved solids (TDS).

In some embodiments, the organic material slurry may have 1,000 ppm-2,000 ppm ammonia, 1,800 ppm-2,500 ppm potassium, and 1,000-1,200 ppm sulfur.

The method may further comprise dosing the digestate with at least one of a coagulant and a flocculant to produce a digestate sludge. The method may comprise separating the digestate sludge from the digestate and combining the digestate sludge with the solids product.

The method may further comprise controlling pH of the filtrate to be between about 9-10.

The method may further comprise controlling pH of the ammonia-depleted filtrate to less be between about 7-9. The method may comprise dosing the ammonia-depleted filtrate with an antiscalant.

The method may further comprise controlling pH of the organic-depleted filtrate to less than about 8. The method may comprise dosing the organic-depleted filtrate with a second antiscalant.

In some embodiments, the ammonia-depleted filtrate may have 10 ppm ammonia or less.

In some embodiments, the organic-depleted filtrate may have 10 ppm calcium or less and 10 ppm magnesium or less.

The method may further comprise separating organic contaminants and divalent anions from the organic containing reject to produce a second organic-depleted filtrate.

The method may further comprise combining the second organic-depleted filtrate with the concentrated retentate to produce a dilute retentate. The method may comprise concentrating the dilute retentate to produce a second concentrated retentate and a second return permeate. The method may comprise directing the second return permeate to dilute the animal organic material. The method may comprise combining the second concentrated retentate with the digestate solids and the organic containing reject.

In some embodiments, the method may comprise processing the biogas to produce natural gas.

The method may comprise using energy generated by the biogas to power at least one operation of the method.

In some embodiments, the method may comprise producing zero liquid discharge.

In accordance with another aspect, there is provided a system for treating an animal organic material comprising solids. The system may comprise a dilution tank having a first inlet fluidly connected to a source of the animal organic material, a second inlet, and an organic material slurry outlet. The system may comprise an anaerobic digester having an inlet fluidly connected to the organic material slurry outlet, a biogas outlet, and a digestate outlet. The system may comprise a first solids-liquid separation subsystem having an inlet fluidly connected to the digestate outlet, at least one digestate solids outlet, and a filtrate outlet. The first solids-liquid separation subsystem may be configured to produce the filtrate having less than 1 ppm total suspended solids (TSS). The system may comprise an ammonia-reducing column having an inlet fluidly connected to the filtrate outlet, a countercurrent source of an acid, and an ammonia-depleted filtrate outlet. The system may comprise a second solids-liquid separation subsystem having an inlet fluidly connected to the ammonia-depleted filtrate outlet, at least one retentate outlet, and at least one return permeate outlet. The second solids-liquid separation subsystem may be configured to produce the return permeate having 200-500 ppm total dissolved solids (TDS). The system may comprise a production water storage tank having an inlet fluidly connected to the at least one return permeate outlet and an outlet fluidly connected to the second inlet of the dilution tank. The system may comprise a solids product holding tank having a first inlet fluidly connected to the at least one digestate solids outlet and a second inlet fluidly connected to the at least one retentate outlet.

In some embodiments, the first solids-liquid separation subsystem may comprise a centrifuge having the inlet fluidly connected to the digestate outlet, a first digestate solids outlet, and a digestate wastewater outlet. The first solids-liquid separation subsystem may comprise a microfiltration unit having an inlet fluidly connected to the digestate wastewater outlet, a second digestate solids outlet, and the filtrate outlet.

The system may comprise at least one of a source of a coagulant and a source of a flocculant positioned upstream from the centrifuge.

In some embodiments, the coagulant and the flocculant are acceptable to produce a certified class A biosolids product.

The system may comprise a first source of a pH adjuster positioned upstream from the ammonia-reducing column.

The system may comprise a second source of a pH adjuster positioned upstream from the second solids-liquid separation subsystem.

The system may comprise a second source of an antiscalant positioned upstream from the second solids-liquid separation subsystem.

In some embodiments, the anaerobic digester may be a continuous stirred tank reactor (CSTR).

In some embodiments, the second solids-liquid separation subsystem may comprise a nanofiltration unit having the inlet fluidly connected to the ammonia-depleted filtrate outlet, a first retentate outlet, and an organic-depleted filtrate outlet. The second solids-liquid separation subsystem may comprise a reverse osmosis unit having an inlet fluidly connected to the organic-depleted filtrate outlet, a second retentate outlet, and a first return permeate outlet.

The system may comprise a third source of a pH adjuster positioned upstream from the reverse osmosis unit.

The system may comprise a second source of an antiscalant positioned upstream from the reverse osmosis unit.

The system may comprise a second nanofiltration unit having an inlet fluidly connected to the first retentate outlet, a third retentate outlet fluidly connected to the solids product holding tank, and a second organic-depleted filtrate outlet.

The system may comprise a second reverse osmosis unit having an inlet fluidly connected to the second retentate outlet and the second organic-depleted filtrate outlet, a fourth retentate outlet fluidly connected to the solids product holding tank, and a second return permeate outlet fluidly connected to the production water storage tank.

In some embodiments, the source of the animal organic material comprises at least one of poultry manure, cow manure, swine manure, goat manure, sheep manure, and horse manure.

The system may comprise a biogas processing unit fluidly connected to the biogas outlet.

The system may be configured to produce zero liquid discharge.

The disclosure contemplates all combinations of any one or more of the foregoing aspects and/or embodiments, as well as combinations with any one or more of the embodiments set forth in the detailed description and any examples.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
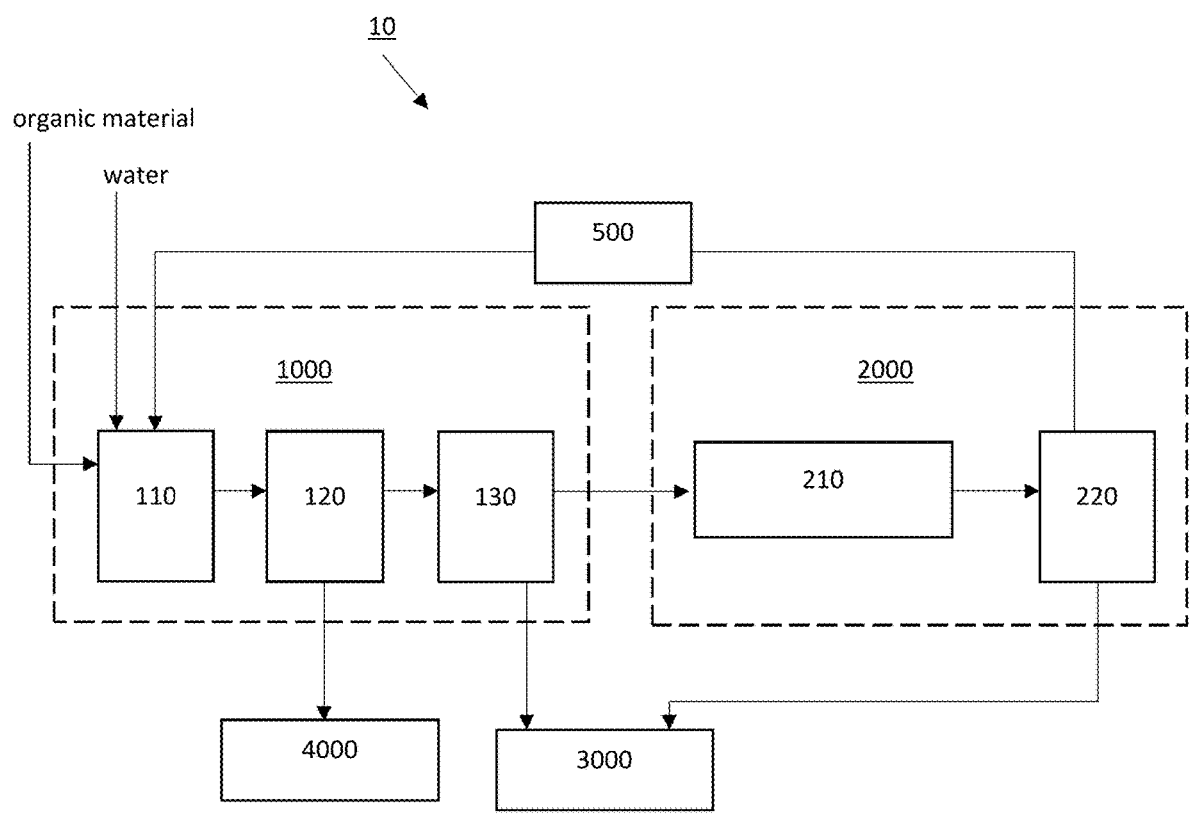
FIG. 1 is a box diagram of a system for treatment of animal organic material, according to one embodiment.

In one aspect, the disclosure relates to a system and method which can be employed to reduce odors and recover biogas and water from animal organic material, such as flushed livestock manure. The system and method disclosed herein may generally relate to anaerobic digestion of animal organic material, such as flushed manure, and reducing or minimizing fresh water consumption. In particular, the amount of fresh water used by the disclosed system and method may be reduced or minimized by recovering and recycling wastewater from the process. The disclosure relates to systems and methods for recovering and recycling the wastewater.

The systems and methods disclosed herein relate to treatment of organic material under anaerobic conditions. During anaerobic treatment, an organic material slurry may be directed to a tank or reactor comprising anaerobic microorganisms. The anaerobic microorganisms convert biologically degradable material in the wastewater primarily into water, biogas, and biosolids. In particular, anaerobic microorganisms facilitate decomposition of macromolecular organic matter into simpler compounds and biogas by methane fermentation. Exemplary anaerobic microorganisms include methanogens and acetogens. The produced biogas is primarily carbon dioxide and methane but may include other constituents depending on the composition of the slurry.

Anaerobic treatment may generally refer to situations in which the prevailing conditions of the slurry within the tank or reactor are anaerobic. The tank or reactor may be closed. The tank or reactor may be open. In particular, even in embodiments in which the anaerobic treatment tank or reactor is open, anaerobic treatment may occur in the absence of added oxygen when the prevailing conditions in the water are anaerobic.

Animal organic material may be treated by anaerobic digestion. Generally, upon storage of the organic material, methanogenic microorganisms found in the organic material initiate the process of degradation producing intermediate compounds which are volatile and often a source of odors. During anaerobic digestion, the growth of methanogens is promoted to convert the intermediate compounds into biogas and nutrient-rich digestate. Microorganism growth may be promoted by addition of microorganisms during start-up and/or dosing with microorganism nutrients. The odor potential of the organic material may be greatly reduced. Methanogenic growth in anaerobic digestion of organic material may be controlled by controlling operating temperature, residence time of the bacteria within the digestor, and/or mixing conditions.

Additionally, the produced biogas may be recovered and converted to heat energy. The heat energy may be used as heat for various processes in the facility. The biogas may be converted to electrical energy with an internal combustion engine.

In addition to biogas recovery, another important factor of the digestion is the minimization of water consumption. The digestion process tends to consume large quantities of water for dilution. The systems and methods disclosed herein may be utilized to treat the process wastewater and recover a percentage of the water to reduce or minimize the amount of fresh water required. Anaerobic digestion of animal organic material may be a batch or semi-continuous processes. For instance, anaerobic digestion may be performed in plug-flow digesters, complete-mix digesters, covered lagoons, or continuously stirred reactors.

Thus, in accordance with one aspect, there are provided systems and methods for treating animal organic material comprising solids. The animal organic material may comprise manure. The animal organic material may comprise litter, for example, fiber or wood materials. The animal organic material may have a solids content of greater than 10%, for example, greater than 15%, greater than 25%, greater than 30%, greater than 35%, greater than 40%, greater than 45%, greater than 50%, greater than 60%, or greater than 75%. The source of the animal organic material may be one or more of poultry manure, cow manure, swine manure, goat manure, sheep manure, and horse manure. In exemplary embodiments, the source of the animal organic material may comprise chicken litter having 70%-80% solids.

The animal organic material may comprise, for example, poultry manure or poultry litter. In some embodiments, the poultry manure or poultry litter may comprise chicken manure or chicken litter. Poultry may generally refer to domestic fowl. In some embodiments, poultry may comprise wild game birds. Poultry manure or litter may comprise chicken, turkey, goose, duck, swan, quail, ostrich, or pigeon manure or litter, and combinations thereof. The animal organic material may comprise animal manure or litter, for example, of any domesticated or farm animal. The organic material may additionally or alternatively comprise sewage sludge. In some embodiments, the organic material may additionally or alternatively comprise food waste, for example, produce waste. Methods disclosed herein may comprise collecting manure, litter, sewage sludge, or food waste. Methods may comprise processing manure, litter, sewage sludge, or food waste to produce an organic material for use in the methods and systems described herein.

The animal organic material may be a nitrogen-rich substrate. The animal organic material may have a total nitrogen (N) content of 17,000-36,000 ppm. The total N may be determined by measuring ammonia nitrogen ($NH_3$—N), organic nitrogen, and nitrate nitrogen ($NO_3^-$—N) of the animal organic material. The animal organic material may be rich in salts. For example, the animal organic material may have 16,000-32,000 ppm potassium, for example, 16,000-23,000 ppm potassium. The animal organic material may have 2,200-4,500 ppm magnesium. The animal organic material may have 13,000-45,000 ppm calcium. The animal organic material may have 6,000-15,000 ppm sulfur. The animal organic material may have 200,000-400,000 mg/L total dissolved solids (TDS), for example, 250,000-350,000 mg/L TDS. The animal organic material may have 300,000-500,000 mg/L total suspended solids (TSS), for example, 350,000-450,000 mg/L TSS. The animal organic material may have 600,000-800,000 mg/L total chemical oxygen demand (COD), for example, 650,000-750,000 mg/L COD.

The method may comprise diluting the animal organic material to produce an organic material slurry. The animal organic material may be diluted with an amount of water sufficient to produce a flowable slurry. The flowable slurry may have a solids content of less than 15%, for example, less than 12%, less than 10%, less than 8%, or less than 6%. In some embodiments, the method may comprise grinding the diluted organic material to produce the slurry.

The animal organic material may be diluted with an amount of water sufficient to dilute the salt content to a concentration safe for anaerobic microorganisms. The concentration safe for microorganisms may be a concentration effective to prevent a significant reduction in viability of the microorganism population. The concentration safe for microorganisms may be a concentration effective to prevent a significant reduction in reproduction, i.e., rate of reproduction of the microorganism population. The concentration safe for microorganisms may be a concentration effective to prevent a significant reduction in digestion, i.e., rate of conversion of organic matter into methane.

The organic material slurry may have less than 2,000 ppm ammonia, for example, 1,000 ppm-2,000 ppm ammonia. In some embodiments, the organic material slurry may have less than 1,000 ppm ammonia. The organic material slurry may have less than 2,500 ppm potassium, for example, 1,800 ppm-2,500 ppm potassium. The organic material slurry may have less than 1,200 ppm sulfur, for example, 1,000-1,200 ppm sulfur.

The dilution water may be fresh water, for example, well water or tap water grade. In some embodiments, the fresh water may have less than 200 ppm TDS, for example, 100-200 ppm TDS, less than 150 ppm TDS, or less than 100 ppm TDS. The dilution water may comprise a return permeate, as described in more detail below. The return permeate may have less than 800 ppm TDS, for example, less than 500 ppm TDS, for example 100-500 ppm TDS or 200-500 ppm TDS.

The dilution water may be a blend of fresh water and return permeate. For instance, the dilution water may have 5:1 to 1:5 fresh water to return permeate. In some embodiments, the dilution water may have 1:1-1:5 fresh water to return permeate, for example, 1:2-1:5, 1:3-1:4, or 1:3-1:5 fresh water to return permeate. The dilution water may have a controlled concentration of salts. In some embodiments, the dilution water may have less than 100 ppm potassium, for example, 10-100 ppm potassium. The dilution water may have less than 100 ppm ammonia, for example, 10-100 ppm ammonia. The dilution water may have less than 100 ppm sulfur, for example, 10-100 ppm sulfur.

The systems and methods disclosed herein may include anaerobically digesting the organic material slurry to produce a biogas and a digestate. Anaerobic digestion includes bringing the organic material slurry into contact with a microorganism population in a substantially anaerobic environment. The anaerobic microorganism population may break down organic matter from the slurry and produce biogas. During anaerobic digestion, organic nitrogen may be converted to ammonia. Temperature of the anaerobic digestion may be controlled. In some embodiments, temperature of the anaerobic digestion may be between, for example, 90-100° F. (32-38° C.) or 95-100° F. (35-38° C.). The anaerobic microorganism mixed liquor within the digester may be agitated, for example, in a continuous stirred tank reactor.

Nutrients and/or alkalinity agents may be supplied to the anaerobic microorganisms, for example, nitrogen, phosphorous, sodium bicarbonate, urea, phosphoric acid, and combinations thereof. Total Kjeldahl Nitrogen (TKN) and ammonia nitrogen ($NH_3$—N) measurements of the digestate may be used to determine whether sufficient nitrogen is available for the digestion process. Phosphate phosphorous ($PO_4$—P) measurements of the digestate may be used to determine whether sufficient phosphorous is available for the digestion process. Thus, the methods may comprise measuring nitrogen content and/or phosphorous content of the digestate. The methods may comprise supplying an effective amount of nutrients and/or alkalinity agents responsive to the digestate measurement.

Residence time of the mixed liquor within the anaerobic digester may be controlled. The organic material slurry may be in contact with the microorganism population for an amount of time sufficient to convert a predetermined amount of organic matter into biogas. In some embodiments, the organic material slurry may be in contact with the microorganism population for an amount of time sufficient to exhaust biogas production from the slurry batch. The hydraulic retention time (HRT) of the mixed liquor in anaerobic digestion may be 15-35 days, for example, 20-30 days, for example, about 15 days, about 20 days, about 25 days, about 30 days, or about 35 days.

The method may comprise collecting the raw biogas produced by the digestion. The raw biogas may comprise methane and carbon dioxide. The raw biogas may comprise water vapor. The raw biogas may comprise additional constituents or nutrients based on the composition of the organic material slurry. In some embodiments, the raw biogas may be at least 40% methane, at least 45% methane, at least 50% methane, for example, at least 55% methane, at least 60% methane, or at least 65% methane. Carbon dioxide may make up a majority of the remainder of the biogas.

The method may comprise measuring flow volume of the raw biogas. The method may comprise measuring composition of the raw biogas produced by the digestion. The composition of the raw biogas may depend on the composition of the animal organic material. For example, the composition of the raw biogas may depend on carbon to nitrogen ratio (C:N), pH, moisture, total solids, temperature, biological oxygen demand (BOD), loading rate, and HRT of the organic material slurry.

The methods may comprise measuring methane content of the raw biogas. The methods may comprise controlling one or more parameter of the digestion responsive to the methane measurement, for example, controlling temperature, mixing conditions, loading rate, or HRT of the digestion responsive to the methane concentration being below a predetermined threshold, for example, below 55%, below 50%, below 45%, or below 40%. The methods may comprise controlling composition of the organic material slurry responsive to the methane measurement, for example, controlling moisture, C:N, pH, total solids, or BOD of the organic material slurry.

Certain parameters may be controlled to increase methane content of the raw biogas. In exemplary embodiments, pH of the organic material slurry may be controlled to be about 6-8. C:N of the organic material slurry may be controlled to be about 20-30:1, for example, 25-30:1. Temperature may be controlled to be 90-100° F. (32-38° C.), for example, 95-100° F. (35-38° C.). Mixing conditions of the mixed liquor within the digester may be controlled.

The systems and methods disclosed herein may use energy generated by the biogas. In some embodiments, energy may be generated by the biogas in the form of heat energy. Heat energy may be captured from the biogas with a boiler or combined heat and power process. The captured heat energy may be used by one or more unit operations of the system. The captured heat energy may be used by a unit operation of the facility. Heat energy may be converted with a heat exchanger loop. For example, heat energy may be transferred to an energy demand with a heat exchanger loop. The energy demand may include one or more unit operations of the system and/or another unit operation of the facility.

In some embodiments, energy may be generated by the biogas in the form of electrical energy. Energy from the biogas may be converted to electrical energy with an internal combustion engine. The electrical energy may be used to operate one or more unit operations of the system and/or another unit operation of the facility.

In some embodiments, the method may comprise processing the raw biogas to produce natural gas. The raw biogas may be refined and converted to natural gas, for example, renewed natural gas (RNG). The refinement process may include removing moisture, carbon dioxide, and trace level contaminants from the raw biogas including, for example, any siloxanes, volatile organic compounds (VOCs), and hydrogen sulfide. The refinement process may include removing nitrogen and oxygen content of the raw biogas. The refinement process may produce a natural gas having a methane content of at least 90%. In some embodiments, the produced natural gas may have a methane content of at least 92%, at least 94%, at least 96%, or at least 98%. The produced natural gas may be injected into a conventional natural gas pipeline or used to replace fossil fuel natural gas in any existing application. For example, the produced natural gas may be used to generate electrical energy. The electrical energy may be used by one or more unit operations of the system and/or a unit operation of the facility.

The digestate produced by the anaerobic digestion may be a sludge containing wastewater. The digestate may comprise 15,000-25,000 ppm total suspended solids (TSS). The digestate may comprise 9,000-20,000 ppm TDS. The digestate may comprise 1,800-2,900 ppm potassium. The digestate may comprise 1,000-1,700 ppm ammonia. The digestate may comprise 1,000-1,600 ppm calcium. The digestate may comprise 100-600 ppm magnesium.

The method may comprise separating the digestate to produce a digestate solids and a filtrate. The digestate solids may retain substantially all of the suspended solids from the digestate and a portion of the dissolved solids. Thus, the separation may reduce TSS of the stream by at least 95%, at least 98%, at least 99%, at least 99.9%, or at least 99.99%. The separation may reduce TDS of the stream by about 30%-65%, for example, about 35%, about 50%, or about 65%. The separation may be performed by one or more of centrifuge separation, thickening, straining, settling, and membrane filtration. The digestate solids may be collected to produce a solids product. The filtrate may be further treated to produce a return permeate, as described below.

The separation of the digestate into digestate solids and a filtrate may comprise dosing the digestate with at least one of a coagulant and a flocculant to produce a digestate sludge. A coagulant may induce coagulation of suspended solids in the digestate. Coagulation may be induced by destabilization of colloidal and dispersed particles, inducing growth to larger particle sizes. Exemplary coagulants include anionic and cationic molecules. A flocculant may induce flocculation of suspended solids in the digestate. Flocculation may be induced by agglomerating solids, such as coagulated solids and other suspended solids, into aggregates or complexes. Exemplary flocculants include high molecular weight polymers having exposed bonding groups to aggregate suspended and coagulated solids. Certain separation additives may act as both coagulants and flocculants. Exemplary separation additives include calcium hydroxide (lime), ferric sulfate, anionic polymers, and cationic polymers. One exemplary separation additive is Alumafloc™ (distributed by Siemens Industry, Inc., Munich, Germany). Thus, the separation may comprise dosing the digestate with one or more of calcium hydroxide, ferric sulfate, an anionic polymer, and a cationic polymer. The digestate sludge comprising the agglomerated solids may be collected to produce the solids product.

In some embodiments, the separation of the digestate into digestate solids and a filtrate may be performed by a series of separations. For example, the separation may comprise dosing the digestate with at least one of a coagulant and a flocculant to produce the digestate sludge comprising large suspended solids. The digestate sludge may be separated from the digestate by at least one centrifuge and/or settling. Remaining suspended solids in the digestate may then be separated by a filter membrane, for example, by microfiltration, to produce the digestate solids and the filtrate. The digestate sludge and the digestate solids may be combined to form the solids product. In some embodiments, the separation may comprise thickening the digestate prior to separation by the centrifugation and/or settling. In some embodiments, the separation may comprise straining the digestate, for example, with a mesh screen, prior to separation by the centrifugation and/or settling. The mesh screen may have average pores between 10-100 µm, for example 50 µm.

In exemplary embodiments, the digestate may be dosed with calcium hydroxide. Calcium hydroxide may induce agglomeration of suspended solids as a coagulant. Calcium hydroxide may also reduce calcium and magnesium concentration of the solution, as a softener. For instance, the methods may comprise dosing the digestate with an amount of calcium hydroxide effective to produce a filtrate with at least 95%, at least 98%, at least 99%, at least 99.9%, or at least 99.99% less calcium and magnesium than the digestate. Additionally, calcium hydroxide may increase pH of the solution. The pH may be controlled for removal of ammonia, as described below.

The methods may comprise returning the one or more dosing agent, for example, coagulant, flocculant, or calcium hydroxide, to an upstream reaction tank. The methods may comprise returning sludge, for example, activated sludge, to the anaerobic digester or an upstream reaction tank.

The systems and methods disclosed herein may comprise recovering water from the filtrate to produce a return permeate for diluting the animal organic material. Recovering water within the system reduces the need for fresh water. The methods may comprise treating the filtrate to produce the return permeate. In some embodiments, the filtrate may have less than 1 ppm TSS. The filtrate may have 4,000-10,000 ppm TDS, for example, 7,000-9,000 ppm TDS. The filtrate may have 1,000-2,100 ppm potassium. The filtrate may have 600-1,100 ppm ammonia.

The methods may comprise controlling pH of the filtrate to less than about 10. For example, the methods may comprise controlling pH of the filtrate to be between about 4 and about 10, between about 7 and about 10, or between about 9 and about 10. The methods may comprise dosing the filtrate with an effective amount of a pH adjuster. The pH adjuster may comprise an acid or a base. Exemplary pH adjusters include strong bases, for example, sulfuric acid, hydrochloric acid, perchloric acid, and nitric acid. Other exemplary pH adjusters include, for example, potassium hydroxide, sodium hydroxide, sodium carbonate, ammonium hydroxide, calcium hydroxide, or magnesium hydroxide. In exemplary embodiments, pH may be controlled to be less than about 10 by dosing the filtrate with an effective amount of sulfuric acid.

The systems and methods disclosed herein may include removal of ammonia from the filtrate to produce an ammonia-depleted filtrate. During anaerobic digestion, temperature and pH of the mixed liquor are generally maintained to favor digestion of organic material into methane gas. Under such conditions, ammonia exists substantially in the ammonium-ion form. After digestion, pH may be controlled to a value effective for removal of ammonia. For example, pH may be controlled to be greater than 9 by addition of an effective amount of one or more pH adjusters. Certain separation additives, for example, coagulants and flocculants, may increase pH of the solution. In such embodiments, pH may be reduced to be below 10 with an acidic pH adjuster. Exemplary pH adjusters are calcium hydroxide and sulfuric acid, as previously described. In one exemplary embodiment, ammonia may be removed by contacting the filtrate with an ammonia reducing column running countercurrent sulfuric acid.

The methods may comprise reducing ammonia of the filtrate by at least about 90%, for example, at least about 95%, at least about 98%, at least about 99%, at least about 99.9%, or at least about 99.99% to produce the ammonia-depleted filtrate. The ammonia-depleted filtrate may comprise less than 100 ppm ammonia, for example, less than 50 ppm ammonia, less than 10 ppm ammonia, less than 5 ppm ammonia, less than 2 ppm ammonia, or less than 1 ppm ammonia. The ammonia-depleted filtrate may have 4,000-10,000 ppm TDS, for example, 7,000-9,000 ppm TDS.

The methods may comprise controlling pH of the ammonia-depleted filtrate to less than about 9, for example, between about 4-9 or 7-9. The pH of the ammonia-depleted filtrate may be controlled by dosing the ammonia-depleted filtrate with an effective amount of a pH adjuster, as previously described.

The methods may comprise dosing the ammonia-depleted filtrate with an antiscalant. The antiscalant may be a silica, sulfate (for example, barium sulfate, calcium sulfate, strontium sulfate), calcium carbonate, and/or calcium fluoride scale inhibitor. Thus, the ammonia-depleted filtrate may be dosed with an effective amount of the antiscalant to inhibit formation of scale on one or more downstream unit operations, for example, a microfiltration unit, a nanofiltration unit, and/or a reverse osmosis unit. In exemplary embodiments, the antiscalant may comprise Vitec® 7400 (distributed by Avista Technologies, Inc., San Marcos, CA).

The methods may comprise dosing the ammonia-depleted filtrate with potassium bisulfite. Potassium bisulfite may be used to neutralize chlorine, chloramines, and residual ammonia in the ammonia-depleted filtrate.

The systems and methods disclosed herein may involve removing organic contaminants and divalent anions from the ammonia-depleted filtrate to produce an organic containing reject and an organic-depleted filtrate. The organic contaminants and divalent anions may be removed by nanofiltration. The organic containing reject may be collected to form the solids product. The organic containing reject and the digestate solids may be combined (with any digestate sludge) to form the solids product. In some embodiments, the organic containing reject may be directed to an upstream reactor, for example, to dilute the animal organic material.

The organic depleted filtrate may have 40-60% less TDS than the ammonia-depleted filtrate, for example, 40-50% less TDS. The organic-depleted filtrate may have 2,000-5, 000 ppm TDS, for example, 3,500-4,500 ppm TDS. The organic-depleted filtrate may have at least 90% less calcium and magnesium than the ammonia-depleted filtrate, for example, at least 90%, at least 95%, at least 98%, at least 99%, at least 99.9%, or at least 99.99% less calcium and magnesium. The organic-depleted filtrate may have 10 ppm calcium or less, for example, 5 ppm calcium or less, or 1 ppm calcium or less. The organic-depleted filtrate may have 10 ppm magnesium or less, for example, 5 ppm magnesium or less, or 1 ppm magnesium or less.

The methods may comprise controlling pH of the organic-depleted filtrate to less than about 8, for example, between about 4-8 or 6-8. The pH of the organic-depleted filtrate may be controlled by dosing the organic-depleted filtrate with an effective amount of a pH adjuster, as previously described.

The method may comprise dosing the organic-depleted filtrate with an antiscalant. The organic-depleted filtrate may be dosed with an effective amount of the antiscalant to inhibit formation of scale on one or more downstream unit operations, for example, a microfiltration unit, a nanofiltration unit, and/or a reverse osmosis unit.

The systems and methods disclosed herein may involve concentrating the organic-depleted filtrate to produce a concentrated retentate and a return permeate. The organic-depleted filtrate may be concentrated by reverse osmosis. The organic-depleted filtrate may be concentrated by brackish reverse osmosis. The methods may comprise concentrating the organic-depleted filtrate between 2×-5×, for example, about 2×, about 3×, about 4×, or about 5×, to produce the concentrated retentate. The concentrated retentate may be collected to form the solids product. The concentrated retentate, organics containing reject, and digestate solids may be combined (with any digestate sludge) to form the solids product.

The return permeate may have at least 90% less TDS than the organic-depleted filtrate, for example, at least 90%, at least 95%, at least 98%, at least 99%, at least 99.9%, or at least 99.99% less TDS. The return permeate may have 10-500 ppm TDS, for example, 100-400 ppm TDS, or 200-300 ppm TDS. The return permeate may be directed to dilute the animal organic material, as previously described.

In some embodiments, to further recover water, organic contaminants and divalent anions may be separated from the organic containing reject to produce a second organic-depleted filtrate. Any second organic containing reject produced may be collected to form the solids product, for example, combined with the digestate solids and any digestate sludge to form the solids product. The organic containing reject may be separated by a second nanofiltration.

The method may comprise controlling pH of the organic containing reject to less than about 9, for example, between about 4-9 or 7-9 before the separation. The pH of the organic containing reject may be controlled by dosing the organic containing reject with an effective amount of a pH adjuster, as previously described. The method may comprise dosing the organic containing reject with an antiscalant before the separation. The organic containing reject may be dosed with an effective amount of the antiscalant to inhibit formation of scale on one or more downstream unit operations, for example, a microfiltration unit, a nanofiltration unit, and/or a reverse osmosis unit.

The method may comprise combining the second organic-depleted filtrate with the concentrated retentate to produce a dilute retentate. The methods may comprise controlling pH of the dilute retentate to less than about 8, for example, between about 4-8 or 6-8. The pH of the dilute retentate may be controlled by dosing the dilute retentate with an effective amount of a pH adjuster, as previously described. The method may comprise dosing the dilute retentate with an antiscalant. The dilute retentate may be dosed with an effective amount of the antiscalant to inhibit formation of scale on one or more downstream unit operations, for example, a microfiltration unit, a nanofiltration unit, and/or a reverse osmosis unit.

The method may comprise concentrating the dilute retentate to produce a second concentrated retentate and a second return permeate. The dilute retentate may be concentrated by reverse osmosis. The dilute retentate may be concentrated by seawater reverse osmosis. The dilute retentate may be concentrated by brine recover reverse osmosis. The methods may comprise concentrating the dilute retentate between 2×-5×, for example, about 2×, about 3×, about 4×, or about 5×, to produce the second concentrated retentate. The second concentrated retentate may be collected to form the solids product. The second concentrated retentate, second organics containing reject, and digestate solids may be combined (with any digestate sludge) to form the solids product.

The second return permeate may have at least 90% less TDS than the dilute retentate, for example, at least 90%, at least 95%, at least 98%, at least 99%, at least 99.9%, or at least 99.99% less TDS. The second return permeate may have 500-1,000 ppm TDS, for example, 600-900 ppm TDS, or 700-900 ppm TDS. The method may comprise directing the second return permeate to dilute the animal organic material.

The method may comprise combining the second return permeate with the return permeate and directing the combined return permeates to dilute the animal organic material. The return permeates may be combined in amounts effective to have 200-500 ppm TDS. For example, the combined return permeates may have 1:5-5:1 return permeate to second return permeate, for example, 2:1-5:1, 3:1-4:1, or 3:1-5:1 return permeate to second return permeate.

In some embodiments, recovered water may be used to clean in place or backwash at least one microfiltration unit, nanofiltration unit, or reverse osmosis unit of the system. For example, return permeate and/or second return permeate (for example, combined return permeates) may be directed to backwash at least one of a microfiltration unit, a nanofiltration unit, or a reverse osmosis unit of the system. The return permeate may be combined with a cleaning agent to form a cleaning fluid. The cleaning agent may comprise, for example, one or more of potassium hydroxide, sulfuric acid, and hydrochloric acid. Clean in place waste may be collected to form the solids product. The clean in place waste, concentrated retentate or second concentrated retentate, organics containing reject or second organics containing reject, and digestate solids may be combined (with any digestate sludge) to form the solids product. In some embodiments, the clean in place waste may be directed to an upstream reaction tank for primary separation.

The systems and methods disclosed herein may reduce the fresh water load required for treatment of animal organic material. In some embodiments, the systems and methods disclosed herein may produce zero liquid discharge. Zero liquid discharge may include methods that recover at least 75% of the fresh water used in the process, for example, at least 80%, at least 85%, at least 90%, at least 92%, at least 95%, at least 98%, at least 99%, at least 99.9%, or at least 99.99% of the fresh water. Recovered water includes any water circulating within the system, for example, as directed to dilute the animal organic material, to perform clean in place, held in a reaction tank, or returned to an upstream reaction tank. Small amounts of water may be retained in the solids product and/or lost to evaporation or as water vapor in the biogas.

The systems and methods disclosed herein may produce a solids product from animal organic material. In some embodiments, the solids product may be treated. For example, the solids product may be dried. Residual moisture may be captured from the drier and returned to the digestion or water recovery processes. The solids product may be used to produce a class A biosolids product. Solids products produced by the disclosed methods may comply with requirements for class A biosolids as established by the United States Environmental Protection Agency (EPA). The solids product may be used as a fertilizer product. The solids product may be supplemented with nutrients and/or fertilizer agents. The solids product may be used as an organic product, for example, a certified product suitable for organic farming. Fertilizer products produced by the disclosed methods may comply with requirements outlined by the Organic Materials Review Institute (OMRI).

In certain embodiments, the dosing agents disclosed herein, for example, coagulant, flocculant, softener, pH adjuster, antiscalant, and cleaning agent, may be acceptable to produce a class A biosolids product. Solids products containing dosing agents produced by the disclosed methods may comply with requirements for class A biosolids as established by the EPA. The dosing agents may be acceptable to produce an organic product, for example, a certified product suitable for organic farming. Fertilizer products containing dosing agents produced by the disclosed methods may comply with requirements outlined by the OMRI.

Thus, in accordance with another aspect, there is provided a system for treating an animal organic material comprising solids. The system may include an organic material digestion subsystem and a water recovery subsystem. The organic material digestion subsystem may be configured to effectively digest the animal organic material and produce a biogas, a digestate solids, and a filtrate. The water recovery subsystem may be configured to treat the filtrate and recover a substantial amount of water from the filtrate (the return permeate). The return permeate may be directed back to the organic material digestion subsystem, reducing the requirement of fresh water for the digestion.

The organic material digestion subsystem may comprise a dilution tank having a first inlet fluidly connected to a source of the animal organic material, a second inlet, and an organic material slurry outlet. The dilution tank may be configured to combine the animal organic material with water to produce the organic material slurry outlet. The dilution tank may be sized to hold at least 500 tons per day of animal organic material, for example 500-600 tons per day, and at least 900 gallons per minute of dilution water, for example, at least 900-1,000 gallons per minute. The dilution tank may comprise a grinder configured to grind the combined organic material and water.

The organic material digestion subsystem may comprise an anaerobic digester having an inlet fluidly connected to the organic material slurry outlet, a biogas outlet, and a digestate outlet. The anaerobic digester may be an enclosed vessel or semi-enclosed vessel housing activated sludge comprising anaerobic microorganisms. The anaerobic digester may comprise a temperature control unit including, for example, a temperature sensor and a heater and/or chiller. The temperature control unit may be configured to control temperature of the mixed liquor within the anaerobic digester. The anaerobic digester may comprise an element for agitating the mixed liquor within the digester. In some embodiments, the anaerobic digester may be a continuous stirred tank reactor (CSTR).

The system may comprise a biogas processing unit fluidly connected to the biogas outlet. The biogas processing unit may include an energy harvesting unit. The energy harvesting unit may include a boiler or combined heat and power process. A heat exchanger and/or heat pump may be used to transfer thermal energy from the energy harvesting unit to an energy demand. In some embodiments, the heat exchanger and/or heat pump can be located onsite. Distance may be minimized between the biogas outlet of the anaerobic digester and the boiler or combined heat and power process to capture as much heat energy as possible. The energy demand may be an onsite energy demand, such as a unit operation of the system, a unit operation of the facility, and/or an ambient heating system of the facility.

The energy harvesting unit may include a combustion engine configured to generate electrical energy. The combustion engine may be located onsite. The combustion engine may be configured to use the biogas or natural gas produced from the biogas as fuel. The combustion engine may be electrically connected to an energy demand, for example, an onsite energy demand. The energy demand may be an off-site energy demand. For example, electrical energy may be generated onsite to serve an off-site energy demand. In some embodiments, the combustion engine may be located off-site.

The biogas processing unit may include a biogas treatment unit. The biogas treatment unit may be configured to refine and convert the biogas to natural gas, as previously described. In some embodiments, the biogas treatment unit may be onsite. In other embodiments, the biogas treatment unit may be remotely located.

The organic material digestion subsystem may comprise a first solids-liquid separation subsystem having an inlet fluidly connected to the digestate outlet, at least one digestate solids outlet, and a filtrate outlet. The first solids-liquid separation subsystem may be configured to produce the digestate solids and the filtrate. The first solids-liquid separation subsystem may comprise one or more of a centrifuge, a clarifier, and a membrane filter. The first solids-liquid separation subsystem may be configured to process about 1,000 gallons per minute of digestate. In certain embodiments, the first solids-liquid separation subsystem may be configured to direct 70-80% of the processed digestate (for example, 700-800 gallons per minute of filtrate) to the water recovery subsystem. The first solids-liquid separation subsystem may be configured to direct 20-30% of the processed digestate (for example, 200-300 gallons per minute of digestate solids) to a solids holding tank.

In some embodiments, the first solids-liquid separation subsystem may comprise a centrifuge having the inlet fluidly connected to the digestate outlet, a first digestate solids outlet, and a digestate wastewater outlet. The centrifuge may be configured to separate suspended solids to the digestate solids outlet and the remaining stream to the digestate wastewater outlet. The organic material digestion subsystem may comprise a source of a separation additive. For example, the organic material digestion subsystem may comprise at least one of a source of a coagulant and a source of a flocculant positioned upstream from the centrifuge. In some embodiments, the solids-liquid separation subsystem may comprise a thickener positioned upstream from the centrifuge. In some embodiments, the solids-liquid separation subsystem may comprise a strainer positioned upstream and/or downstream from the centrifuge. The centrifuge may be configured to separate aggregated solids as a digestate sludge from the digestate.

In one exemplary embodiment, the first solids-liquid separation subsystem may comprise a source of calcium hydroxide positioned upstream from a first centrifuge. The first solids-liquid separation subsystem may comprise a source of an anionic polymer also positioned upstream from the first centrifuge. The first centrifuge may be configured to separate the digestate into a first digestate sludge and a first digestate wastewater. The first solids-liquid separation subsystem may comprise a source of ferric sulfate positioned upstream from a concentration tank. The first solids-liquid separation subsystem may comprise a source of a cationic polymer positioned upstream from the concentration tank. The concentration tank may be configured to separate the first digestate wastewater into a second digestate sludge and a second digestate wastewater.

The first solids-liquid separation subsystem may comprise a microfiltration unit. The microfiltration unit may have an inlet fluidly connected to the digestate wastewater outlet (or a second or subsequent digestate wastewater outlet), a digestate solids outlet, and a filtrate outlet. The microfiltration unit may be a membrane filter, a hollow fiber membrane filter, a plate and frame membrane filter, a spiral membrane, a dead end filter, a cross-flow filter, or any other type of filter having pores dimensioned to perform microfiltration. The average pore size of the microfiltration membrane may be 1 to 100 μm, for example 10 to 50 μm. The microfiltration unit may be configured to separate the digestate wastewater into digestate solids and the filtrate. The microfiltration unit may be configured to process 700-800 gallons per minute of fluid.

The first solids-liquid separation subsystem may comprise a source of ferric sulfate positioned upstream from a second centrifuge. The first solids-liquid separation subsystem may comprise a source of an anionic polymer also positioned upstream from the second centrifuge. The second centrifuge may be configured to separate the second digestate sludge into a third digestate sludge and a third digestate wastewater. The third digestate wastewater may comprise a dosing agent or separation additive return. Thus, the third digestate wastewater may be fluidly connected to an upstream reactor, for example, upstream from the first centrifuge or the concentration tank. The third digestate sludge may be directed to the solids holding tank.

The system may comprise a solids product holding tank fluidly connected to the at least one digestate solids outlet (and any digestate sludge outlets) of the first solids-liquid separation subsystem. In some embodiments, the system may comprise a solids return configured to direct separated solids to an upstream reaction tank, for example, to the anaerobic digester or any other upstream reaction tank. The system may comprise a dosing agent holding tank. The dosing agent holding tank may be configured to capture dosing agents, for example, coagulant, flocculant, pH adjusters, or others for reuse. The dosing agent holding tank may be fluidly connected to an upstream reactor.

The water recovery subsystem may comprise an ammonia-reducing column having an inlet fluidly connected to the filtrate outlet, a countercurrent source of an acid, and an ammonia-depleted filtrate outlet. The ammonia-reducing column may be configured to strip ammonia from the filtrate and produce an ammonia-depleted filtrate. The column may comprise a hollow fiber. In exemplary embodiments, the filtrate may flow through the shell-side of the hollow fiber (outside), while the acid solution may flow countercurrent through the lumen-side of the hollow fiber (inside). The countercurrent acid may be sulfuric acid. In such embodiments, the ammonia stripped from the column may be in the form of ammonium sulfate. Any captured ammonium sulfate may be collected for the solids product.

In exemplary embodiments, the ammonia-reducing column may be a Liqui-Cel® membrane contactor (distributed by 3M, Saint Paul, MN).

The water recovery system may comprise a source of a pH adjuster positioned upstream from the ammonia-reducing column. The source of the pH adjuster may be an acid or a base. In one exemplary embodiment, the source of the pH adjuster may comprise sulfuric acid.

The water recovery subsystem may comprise a second solids-liquid separation subsystem having an inlet fluidly connected to the ammonia-depleted filtrate outlet, at least one retentate outlet, and at least one return permeate outlet. The second solids-liquid separation subsystem may be configured to treat the ammonia-depleted filtrate to produce the concentrated retentate and the return permeate. The return permeate may be directed to the dilution tank.

The second solids-liquid separation subsystem may comprise a nanofiltration unit having an inlet fluidly connected to the ammonia-depleted filtrate outlet, a first retentate outlet, and an organic-depleted filtrate outlet. The nanofiltration unit may be a membrane filter, a hollow fiber membrane filter, a plate and frame membrane filter, a spiral membrane, a dead end filter, a cross-flow filter, or any other type of filter having pores dimensioned to perform nanofiltration. The average pore size of the nanofiltration membrane may be 1 to 100 nm, for example 1 to 10 nm. The nanofiltration unit may be configured to separate the ammonia-depleted filtrate into an organic containing reject containing organic contaminants and divalent anions and an organic-depleted filtrate.

The water recovery subsystem may comprise a second source of a pH adjuster positioned upstream from the second solids-liquid separation subsystem, for example, positioned upstream from the nanofiltration unit. The second source of the pH adjuster may be an acid or a base. In one exemplary embodiment, the second source of the pH adjuster may comprise sulfuric acid. The system may additionally or alternatively comprise a source of an antiscalant positioned upstream from the second solids-liquid separation subsystem, for example, upstream from the nanofiltration unit.

The second solids-liquid separation subsystem may comprise a reverse osmosis unit having an inlet fluidly connected to the organic-depleted filtrate outlet, a second retentate outlet, and a first return permeate outlet. A reverse osmosis unit may employ a partially permeable membrane to separate ions and other small molecules from a stream under pressure. The reverse osmosis unit may be a brackish water reverse osmosis unit. The brackish water reverse osmosis unit may operate under a pressure of about 200 psi. The reverse osmosis unit may be configured to concentrate the organic containing reject and produce a concentrated retentate comprising dissolved solids and a return permeate.

The water recovery system may comprise a third source of a pH adjuster positioned upstream from the reverse osmosis unit. The second source of the pH adjuster may be an acid or a base. In one exemplary embodiment, the second source of the pH adjuster may comprise sulfuric acid. The water recovery subsystem may additionally or alternatively comprise a second source of an antiscalant positioned upstream from the reverse osmosis unit. The water recovery subsystem may additionally or alternatively comprise a source of potassium bisulfite positioned upstream from the reverse osmosis unit.

The solids product holding tank may have second inlet fluidly connected to the at least one retentate outlet of the second solids-liquid separation tank, for example, a retentate outlet of the nanofiltration unit and/or a retentate outlet of the reverse osmosis unit. In certain embodiments, the retentate outlet of the nanofiltration unit may be fluidly connected to the dilution tank.

The system may comprise a production water storage tank having an inlet fluidly connected to the at least one return permeate outlet and an outlet fluidly connected to the second inlet of the dilution tank. The production water storage tank may be configured to direct return permeate from the water recovery subsystem back to the organic material digestion subsystem.

In some embodiments, the water recovery subsystem may comprise a second nanofiltration unit having an inlet fluidly connected to the retentate outlet of the first nanofiltration unit, a third retentate outlet, and a second organic-depleted filtrate outlet. The second nanofiltration unit may be configured to separate the organic containing reject to produce a second organic containing reject and a second organic depleted filtrate. The second organic depleted reject may be directed to the solids product holding tank.

The water recovery system may comprise a fourth source of a pH adjuster positioned upstream from the second nanofiltration unit. The fourth source of the pH adjuster may be an acid or a base. In one exemplary embodiment, the fourth source of the pH adjuster may comprise sulfuric acid. The water recovery subsystem may additionally or alternatively comprise a third source of an antiscalant positioned upstream from the second nanofiltration unit.

The water recovery subsystem may further comprise a second reverse osmosis unit having an inlet fluidly connected to the second retentate outlet of the first reverse osmosis unit and the second organic-depleted filtrate outlet of the second nanofiltration unit, a fourth retentate outlet fluidly connected to the solids product holding tank, and a second return permeate outlet fluidly connected to the production water storage tank. The second reverse osmosis unit may be a seawater reverse osmosis unit. The seawater reverse osmosis unit may be configured to operate under a pressure of about 1,000 psi. The second reverse osmosis unit may be a brine recover reverse osmosis unit. The second reverse osmosis unit may be configured to concentrate a dilute retentate (formed by the combination of the concentrated retentate and the second organic-depleted filtrate) and produce a second concentrated retentate comprising dissolved solids and a second return permeate. The second concentrated retentate may be directed to the solids product holding tank. The second return permeate may be directed to the production water storage tank to be combined with the return permeate from the first reverse osmosis unit.

The water recovery subsystem may comprise a fifth source of a pH adjuster positioned upstream from the second reverse osmosis unit. The fifth source of the pH adjuster may be an acid or a base. In one exemplary embodiment, the fifth source of the pH adjuster may comprise sulfuric acid. The water recovery subsystem may additionally or alternatively comprise a fourth source of an antiscalant positioned upstream from the second reverse osmosis unit.

In some embodiments, the system may comprise an ultra-high pressure apparatus (UHP) positioned downstream from the concentrated retentate outlet or the second concentrated retentate outlet. Concentrated retentate may be directed to the influent of the UHP apparatus to further concentrate ionic species, producing liquid stream and a concentrate stream. The system may comprise a crystallizer positioned downstream from the concentrate outlet of the UHP apparatus. The concentrate from the UHP apparatus may be directed to the crystallizer, which is configured to further separate liquids and solids from the concentrate. The distillate from the UHP apparatus may be directed to the product water holding tank. The solids from the crystallizer may be directed to a further dewatering process, such as a filter press, configured to produce a liquid and a sludge cake. The sludge cake may be directed to the solids product holding tank.

The system may comprise a solids product treatment subsystem. The solids product treatment subsystem may be positioned onsite, downstream from the solids product holding tank. The solids product treatment subsystem may be positioned at a remote location. The solids product treatment subsystem may be configured to process the solids product to produce a class A biosolids product. The solids product treatment subsystem may be configured to process the solids product to produce a fertilizer product. In some embodiments, the solids product treatment subsystem may comprise a drier. The solids product treatment subsystem may comprise a source of nutrients and/or fertilizer agent.

The system may comprise one or more clean in place water holding tanks. The clean in place water holding tank may be fluidly connected to the production water storage tank. The clean in place water holding tank may direct recovered water, for example, return permeate, or cleaning fluid, for example, recovered water dosed with at least one cleaning agent, to backwash the at least one microfiltration unit, nanofiltration unit, or reverse osmosis unit of the system to perform a clean in place operation. The clean in place water storage tank may be fluidly connected to a source of a cleaning agent. The clean in place water storage tank may be configured to direct clean in place waste to the solids product holding tank. In some embodiments, the clean in place water storage tank may be configured to direct the clean in place waste to an upstream reactor for separation to the solids product holding tank, for example, by centrifuge or settling.

The system may comprise one or more pumps or valves configured to direct fluid through the unit operations. The system may comprise one or more sensors, for example, composition sensors, configured to measure composition of one or more fluid. The system may comprise one or more pH sensors configured to measure pH of one or more fluid. In some embodiments, the system may comprise a digestate composition sensor. The sensor may be configured to measure one or more of TKN, $NH_3$—N, and $PO_4$—P of the digestate. In some embodiments, the system may comprise a biogas composition sensor. The sensor may be configured to measure methane content of the biogas. In some embodiments, the system may comprise a biogas flow volume sensor. In some embodiments, the system may comprise an organic material slurry composition sensor. The sensor may be configured to measure one or more of pH, total solids, BOD, and C:N of the organic material slurry.

The system may comprise a controller operably connected to the one or more sensor and configured to alert a user responsive to the sensor measuring a value outside tolerance of a predetermined range. The controller may be operably connectable to the one or more pumps or valves. For example, the controller may be configured to direct administration of a dosing agent responsive to a measured value, for example, a measured pH unit. In some embodiments, the controller may be operably connectable to the temperature control unit of the anaerobic digester. The controller may be operably connectable to the stirrer of the anaerobic digester.

The controller may be operably connectable to components associated with the dilution of the animal organic material, for example, pumps and valves for the return water and fresh water and any grinder or agitator of the dilution tank.

In exemplary embodiments, the controller may be configured to dose the organic material slurry with nutrients and/or alkalinity agents responsive to the composition of the digestate, for example, TKN, $NH_3$—N, and/or $PO_4$—N concentration of the digestate. In some embodiments, the controller may be configured to modify the dilution of the animal organic material responsive to the methane content of the biogas, flow volume of the biogas, or composition of the organic material slurry. For instance, the controller may be configured to control ratio of return permeate to fresh water and/or control moisture of the organic material slurry to modify pH, C:N, BOD, and/or total solids content of the organic material slurry. In some embodiments, the controller may be configured to modify mixing conditions of the anaerobic digester responsive to the methane content of the biogas or flow volume of the biogas.

The controller may be a computer or mobile device. The controller may comprise a touch pad or other operating interface. For example, the controller may be operated through a keyboard, touch screen, track pad, and/or mouse. The controller may be configured to run software on an operating system known to one of ordinary skill in the art. The controller may be electrically connected to a power source. The controller may be digitally connected to the one or more components. The controller may be connected to the one or more components through a wireless connection. For example, the controller may be connected through wireless local area networking (WLAN) or short-wavelength ultra-high frequency (UHF) radio waves. The controller may further be operably connected to any additional pump or valve within the system, for example, to enable the controller to direct fluids or additives as needed. The controller may be coupled to a memory storing device or cloud-based memory storage.

Multiple controllers may be programmed to work together to operate the system. For example, a controller may be programmed to work with an external computing device. In some embodiments, the controller and computing device may be integrated. In other embodiments, one or more of the processes disclosed herein may be manually or semi-automatically executed.

Referring to FIG. 1, a system 10 for treatment of animal organic material is shown. The system 10 comprises an organic material digestion subsystem 1000 and a water recovery subsystem 2000. The organic material digestion subsystem 1000 comprises a dilution tank 110 configured to receive the animal organic material and water, an anaerobic digester 120, and a solids-liquid separation subsystem 130. The water recovery subsystem 2000 comprises an ammonia-reducing column 210 and a second solids-liquid separation subsystem 220. The organic material digestion subsystem 1000 and the water recovery subsystem 2000 have solids outlets fluidly connected to solids product subsystem 3000 comprising a holding tank. The solids product subsystem 3000 may comprise a solids product treating subsystem. Biogas produced by the anaerobic digester 120 is directed to a biogas processing subsystem 4000. The biogas processing subsystem 4000 may comprise an energy harvesting unit and/or a biogas treatment unit. The water recovery subsystem 2000 has a return permeate outlet configured to direct recovered water to a production water storage tank 500 fluidly connected to the dilution tank 110. The system 10 may be operated to recover water from the digestion process and produce minimal liquid waste.

Figure 2A:
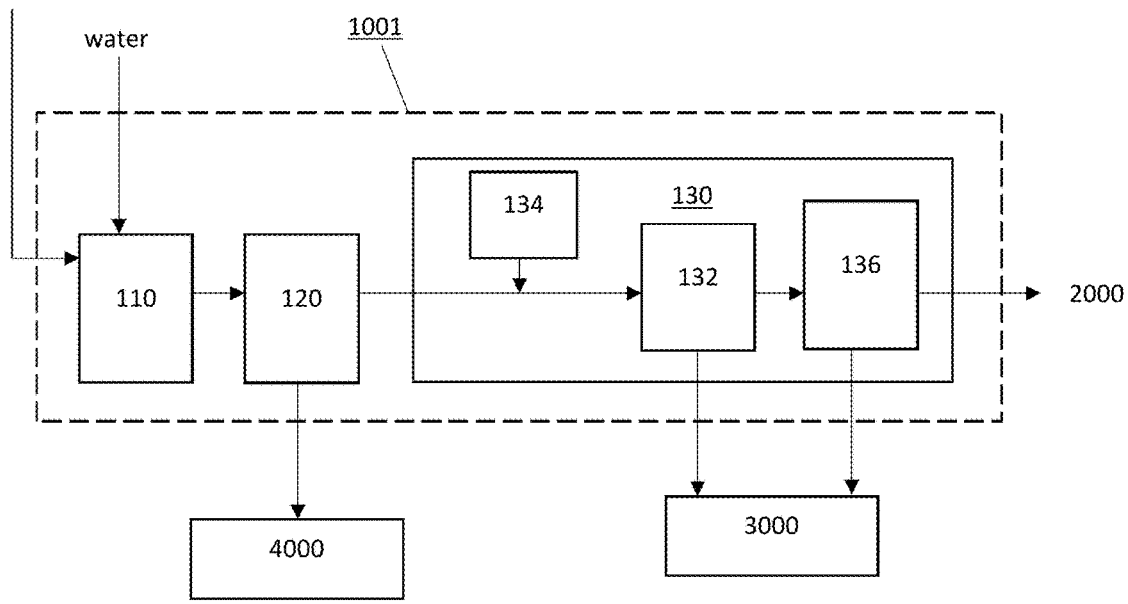
FIG. 2A is a box diagram of a portion of a system for treatment of animal organic material, according to one embodiment.

Referring to FIG. 2A, an exemplary organic material digestion subsystem 1001 is shown. The organic material digestion subsystem 1001 includes dilution tank 110, anaerobic digester 120, and solids-liquid separation subsystem 130. Solids-liquid separation subsystem 130 includes source of a separation additive 134 and centrifuge 132. The separation additive may be a coagulant and/or a flocculant. The separation additive may comprise, for example, calcium hydroxide, ferric sulfate, an anionic polymer, and/or a cationic polymer. Solids-liquid separation subsystem 130 includes microfiltration unit 136 positioned downstream from the centrifuge 132. Solids from the centrifuge 132 and microfiltration unit 136 are directed to the solids product subsystem 3000. Filtrate from the microfiltration unit 136 is directed to the water recovery subsystem 2000. Biogas from the anaerobic digester 120 is directed to the biogas processing subsystem 4000.

Figure 2B:
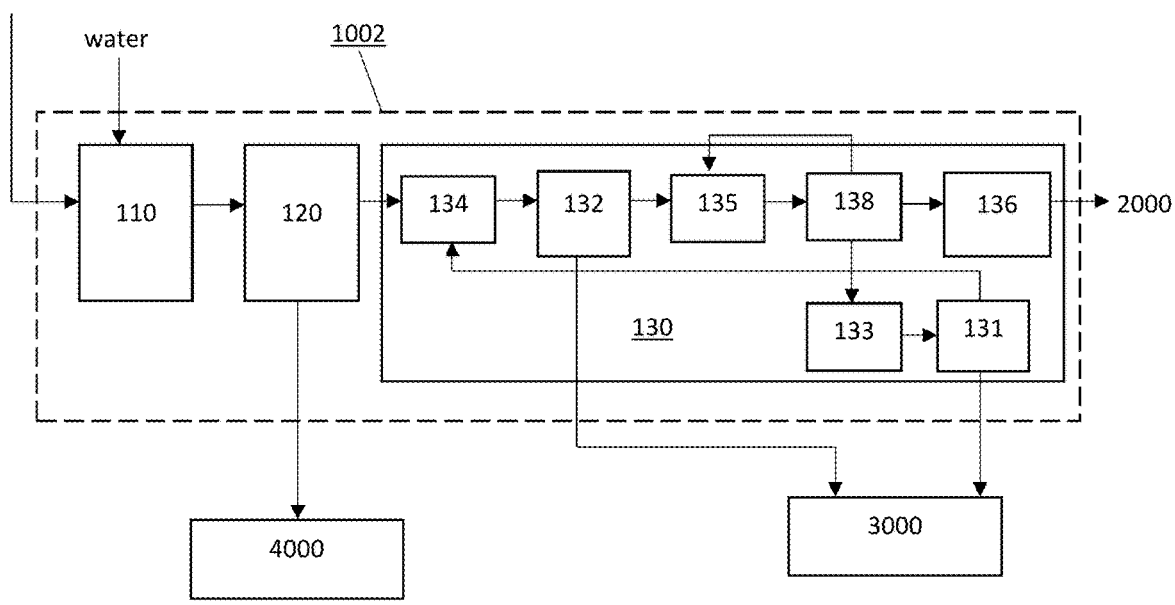
FIG. 2B is a box diagram of a portion of a system for treatment of animal organic material, according to one embodiment.

Referring to FIG. 2B, an alternate exemplary organic material digestion subsystem 1002 is shown. The organic material digestion subsystem 1002 is similar to organic material digestion subsystem 1001, except that the solids-liquid separation subsystem 130 includes, downstream from centrifuge 132 and upstream from microfiltration unit 136, a second source of a separation additive 135 and a concentration tank 138. Solids-liquid separation subsystem 130 also includes third source of a separation additive 133 and second centrifuge 131 positioned downstream from a solids outlet of the concentration tank 138. The concentration tank 138 has a sludge return back to the reactor tank of the second source of a separation additive 135. The second centrifuge 131 has a wastewater outlet fluidly connected to a separation additive return back to the source of separation additive 134. Second centrifuge 131 has a sludge outlet directed to the solids product subsystem 3000.

Figure 3A:
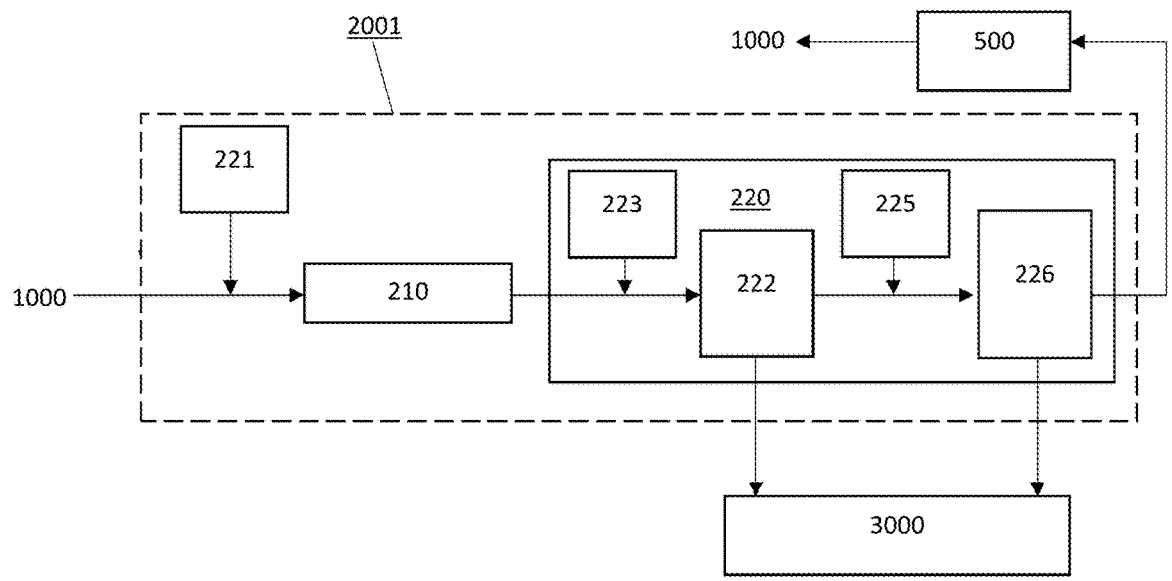
FIG. 3A is a box diagram of a portion of a system for treatment of animal organic material, according to one embodiment.

Referring to FIG. 3A, an exemplary water recovery subsystem 2001 is shown. Water recovery subsystem 2001 includes ammonia reducing column 210 and solids-liquid separation subsystem 220. Water recovery subsystem 2001 includes a first source of a dosing agent 221 positioned upstream from ammonia reducing column 210. Solids-liquid separation subsystem 220 includes a second source of a dosing agent 223, nanofiltration unit 222, a third source of a dosing agent 225, and reverse osmosis unit 226. The dosing agent may comprise, for example, a pH adjuster, and antiscalant, and/or potassium bisulfite. Reverse osmosis unit 226 includes a return permeate outlet directed to production water storage tank 500. Nanofiltration unit 222 and reverse osmosis unit 226 have retentate outlets directed to solids product subsystem 3000.

Figure 3B:
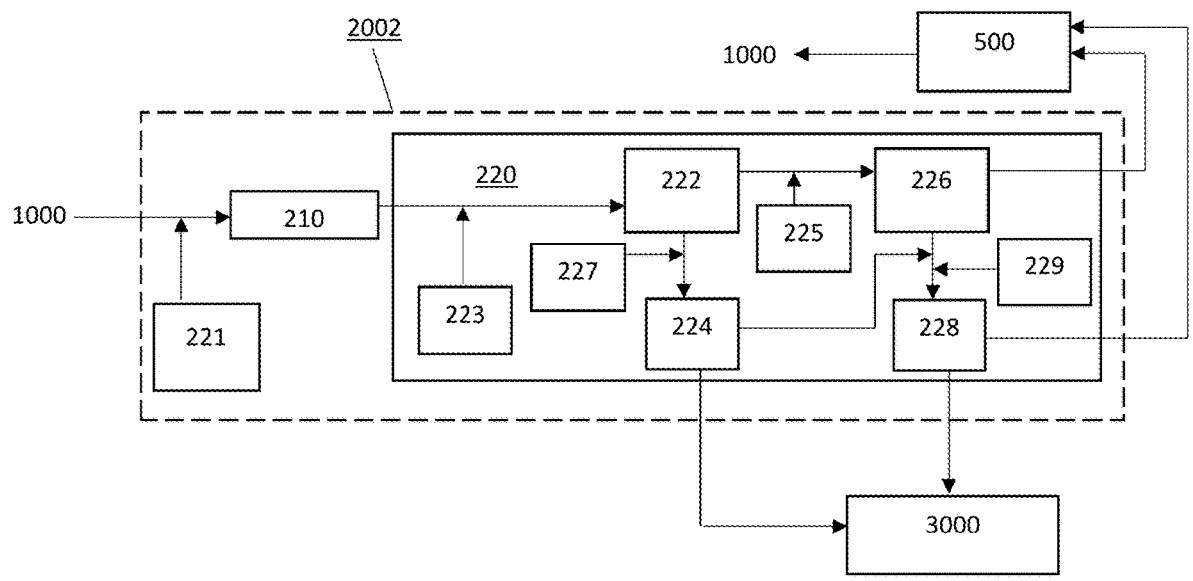
FIG. 3B is a box diagram of a portion of a system for treatment of animal organic material, according to one embodiment.

Referring to FIG. 3B, an alternate exemplary water recovery subsystem 2002 is shown. Water recovery subsystem 2002 is similar to water recovery subsystem 2001, except that the solids-liquid separation subsystem 220 includes fourth source of a dosing agent 227 and second nanofiltration unit 224 positioned downstream from the retentate outlet of the first nanofiltration unit 222. Solids-liquid separation subsystem 220 also includes a fifth source of a dosing agent 229 and second reverse osmosis unit 228 positioned downstream from the retentate outlet of the first reverse osmosis unit 228. Second nanofiltration unit 224 has a filtrate outlet directed to second reverse osmosis unit 228. Second reverse osmosis unit 228 has a return permeate outlet directed to production water storage tank 500. Second nanofiltration unit 224 and second reverse osmosis unit 228 have retentate outlets directed to solids product subsystem 3000.

Figure 4:
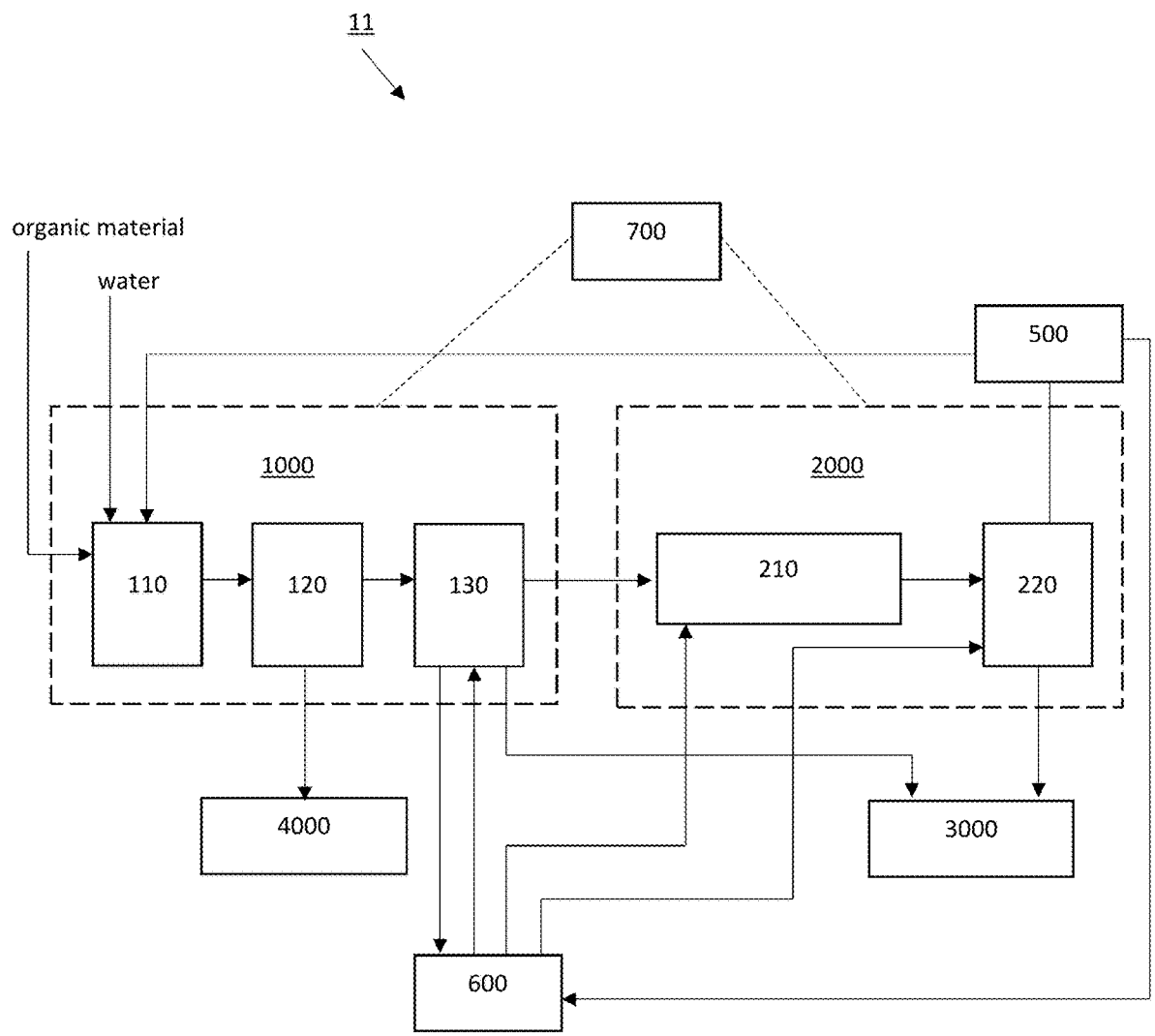
FIG. 4 is a box diagram of a system for treatment of animal organic material, according to one embodiment.

Referring to FIG. 4, system 11 for treatment of animal organic material is shown. System 11 is similar to system 10 except that it includes clean in place tank 600 fluidly connected downstream from production water storage tank 500. Clean in place tank 600 is configured to direct cleaning fluid to solids-liquid separation subsystem 130 (for example, to clean a microfiltration unit) and to solids-liquid separation subsystem 220 (for example, to provide make-up water to an ammonia reducing column, or provide cleaning fluid a nanofiltration unit or reverse osmosis unit). Clean in place tank 600 is configured to direct clean in place waste to solids liquid separation subsystem 130 (for example, to a reaction tank, for centrifuge or settling separation). System 11 also includes controller 700. Controller 700 may be operatively connected to one or more pump, valve, or sensor of the system and configured to direct fluid (for example, administer a separation additive or dosing agent) or control temperature within the system (for example, with a temperature control unit of the anaerobic digester).

EXAMPLES

The function and advantages of these and other embodiments can be better understood from the following examples. These examples are intended to be illustrative in nature and are not considered to be limiting the scope of the invention.

Figure 5:
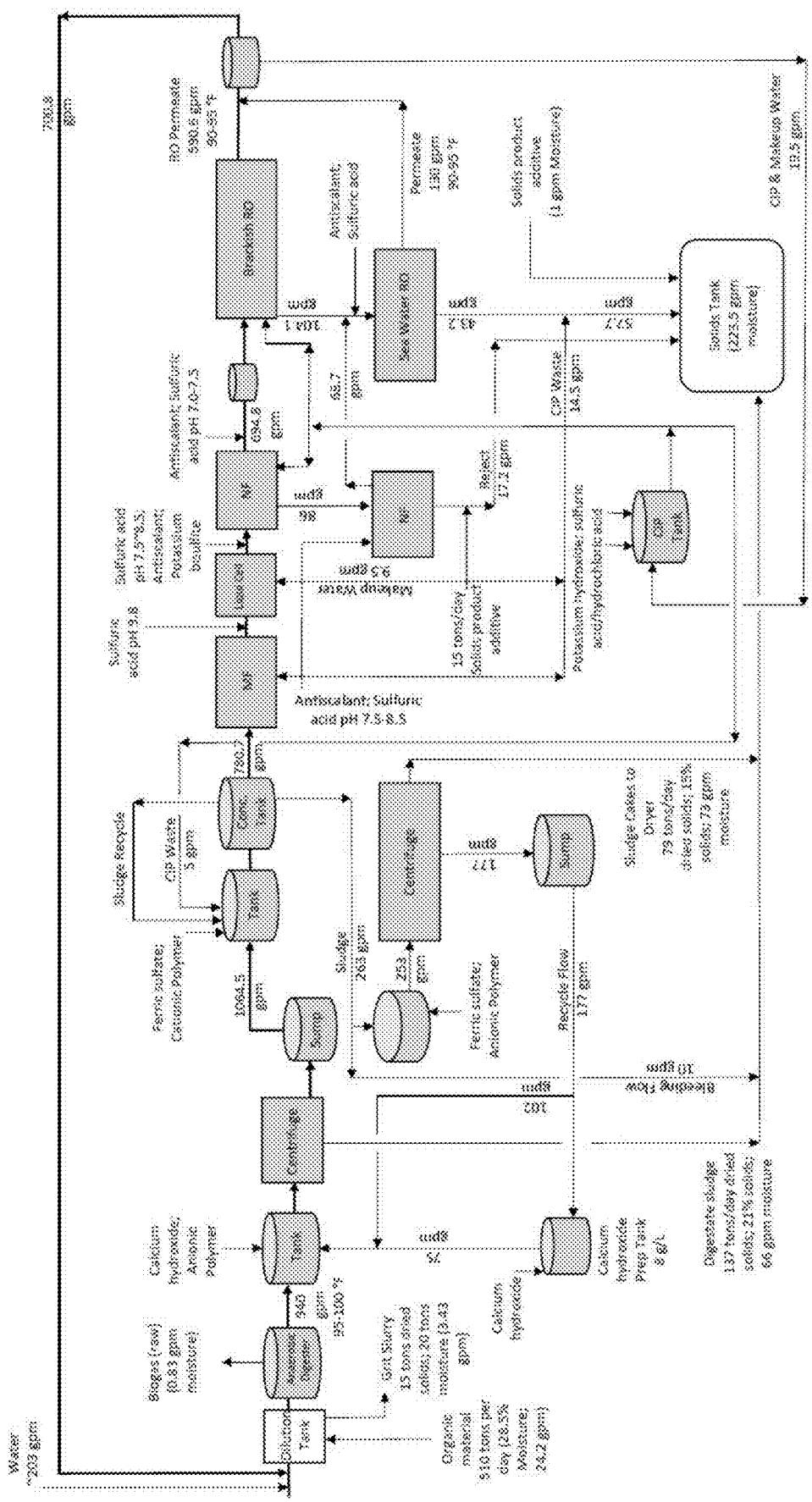
FIG. 5 is a mass balance schematic drawing of a system for treatment of animal organic material, according to one embodiment.

Example 1: Mass Balance of a Zero Liquid Discharge System for Treatment of Animal Organic Material A pilot plant for treatment of animal organic material has been designed. The pilot plant will process approximately 510 tons per day of organic material having about 28.5% moisture at approximately 24.2 gallons per minute (gpm). FIG. 5 is a schematic diagram and mass balance of the pilot plant.

The organic material will be combined with approximately 203 gpm of fresh water (for example, well water) and 700.8 gpm of return permeate in a dilution tank. The organic material slurry will be directed to an anaerobic digester, which will produce raw biogas having approximately 0.83 gpm moisture. Grit slurry having approximately 15 tons dried solids and 20 tons moisture (3.43 gpm) from the dilution tank may be discarded. Together, the grit slurry and biogas contribute to about 4.26 gpm lost moisture.

Approximately 940 gpm digestate will be directed to a reaction tank and dosed with calcium hydroxide and anionic polymer. The calcium hydroxide may be at least partially provided by a calcium hydroxide return tank. The dosed digestate will be directed to a centrifuge, which will separate about 137 tons per day of dried solids having about 66 gpm moisture and about 1,064.5 gpm of a digestate wastewater. The digestate wastewater will be directed to a reaction tank and dosed with ferric sulfate and cationic polymer. The dosed digestate wastewater will be directed to a concentration tank. Sludge will be recycled from the concentration tank to the upstream reaction tank. Approximately 253 gpm of digestate sludge will be directed to a reaction tank and dosed with ferric sulfate and anionic polymer.

About 10 gpm of digestate sludge will be bled to combine with the digestate sludge. The digestate sludge will be directed to a solids holding tank. Approximately 780.7 gpm of digestate wastewater from the concentration tank will be directed to a microfiltration unit. The dosed digestate sludge will be directed to a centrifuge and separated into approximately 177 gpm of a recycle dosed sludge and approximately 79 tons per day of a sludge cake having 73 gpm moisture. The recycle dosed sludge may be directed to an upstream reaction tank, such as the calcium hydroxide return tank. The sludge cake will be directed to the solids holding tank.

The microfiltration unit will separate the digestate wastewater into a digestate solids and a filtrate. The digestate solids will be directed to the solids holding tank. The filtrate will be dosed with sulfuric acid as a pH adjuster and directed to an ammonia reducing column, shown as a Liqui Cell on FIG. 5. The ammonia reducing column will strip ammonia from the filtrate to produce an ammonia-depleted filtrate. The ammonia-depleted filtrate will be dosed with sulfuric acid as a pH adjuster, and antiscalant, and potassium bisulfite. The dosed ammonia-depleted filtrate will be directed to a nanofiltration unit which will separate the ammonia-depleted filtrate into approximately 86 gpm of an organic containing reject and approximately 694.8 gpm of an organic-depleted filtrate.

The organic-depleted filtrate will be dosed with an antiscalant and sulfuric acid as a pH adjuster and directed to a brackish reverse osmosis unit. The brackish reverse osmosis unit will separate the organic-depleted filtrate into approximately 104.1 gpm of a concentrated retentate and approximately 590.6 gpm of a return permeate. The return permeate will be directed to a product water holding tank.

The organic containing reject will be dosed with an antiscalant and sulfuric acid as a pH adjuster and directed to a second nanofiltration unit. The second nanofiltration unit will separate the dosed organic containing reject into approximately 17.2 gpm of a second organic containing reject and approximately 68.7 gpm of a second organic-depleted filtrate. The concentrated retentate from the brackish reverse osmosis unit will be combined with the second organic-depleted filtrate and dosed with an antiscalant and sulfuric acid as a pH adjuster. The dosed and combined retentate will be directed to a seawater reverse osmosis unit and be separated into approximately 43.2 gpm of a second concentrated retentate and approximately 130 gpm of a second return permeate. The second return permeate will be combined with the first return permeate in the product water holding tank and approximately 700.8 gpm of the combined return permeate will be directed to the dilution tank. The solids product holding tank will contain about 223.5 gpm moisture. A solids product additive may be combined with the solids product.

Approximately 19.5 gpm of return permeate will be directed to a clean in place (CIP) tank. The CIP return permeate will be combined with potassium hydroxide, sulfuric acid, and hydrochloric acid to product a cleaning fluid. The cleaning fluid may be directed to the microfiltration unit, the nanofiltration units, and the reverse osmosis units for cleaning. Waste from the clean in place may be directed to an upstream reaction tank to be separated to the solids holding tank.

Accordingly, the process may continue with approximately 720 gpm of recycled water (return permeate and clean in place), with a loss of about 225 gpm moisture in the solids product and less than 5 gpm moisture loss in the biogas and grit slurry. The continuous process may require only about 200 gpm of fresh water. Approximately 75% of the moisture is recycled. Further optimizations may be performed to reduce moisture loss.

Example 2: Digestion of Animal Organic Material

Ten organic material samples from chicken litter were anaerobically digested. The digestates were dosed with varying separation additives. Sample 1 was dosed with 6.5 g/L calcium hydroxide and 0.4 g/L ferric sulfate; samples 2 and 3 were dosed with 8.8 g/L calcium hydroxide and 400 mg/L ferric sulfate; sample 4 was dosed with 9.278 g/L calcium hydroxide and 400 mg/L ferric sulfate; sample 5 was dosed with 8 g/L calcium hydroxide and 400 mg/L ferric sulfate; sample 6 was not dosed; and sample 8 was dosed with 1 g/L ferric sulfate and 25 mg/L cationic polymer. Solids were separated from the dosed digestates by centrifugation and microfiltration to simulate the organic material digestion subsystem. Properties of the select samples were tested after digestion and after microfiltration. The measured values are shown in Tables 1-2, respectively.

TABLE 1

Parameters after Digestion

| Parameter | Sample 1 | Sample 2 | Sample 3 | Sample 4 | Sample 5 |
|---|---|---|---|---|---|
| Calcium (mg/L) | 1200 | 1360 | 1090 | 1440 | 1340 |
| Magnesium (mg/L) | 357 | 455 | 189 | 373 | 383 |
| Sodium (mg/L) | 761 | 854 | 674 | 834 | 829 |
| Potassium (mg/L) | 1860 | 2050 | 2340 | 2710 | 2710 |
| Aluminum (mg/L) | 78 | 84.8 | 50.2 | 84.6 | 97.1 |
| Barium (mg/L) | 2.6 | 2.3 | 1.31 | 1.71 | 1.47 |
| Strontium (mg/L) | 3.37 | 4.25 | 2.64 | 4.28 | 4.27 |
| $NH_4$-N (mg/L) | 1676 | 1270 | 1280 | 1591 | 1440 |
| Copper (mg/L) | 36 | 42.7 | 31.1 | 40.4 | 40.6 |
| Zinc (mg/L) | 41.1 | 43.7 | 26.4 | 35.4 | 38.3 |
| Phosphate-P (mg/L) | 782 | 996 | | 918 | 882 |
| TKN (mg/L) | | 2700 | | 2260 | |
| pH (units) | 8.05 | 7.73 | 7.71 | 7.72 | 7.73 |
| Iron (mg/L) | 168 | 135 | 58 | 69.1 | 71.2 |
| Manganese (mg/L) | 34.1 | 40.5 | 28.5 | 38.4 | 43.9 |
| Silicon (mg/L) | 96 | 115 | 82 | 111 | 128 |
| Total Solids (mg/L) | 27800 | 30300 | | 28750 | 28775 |
| TDS (mg/L) | | | 11300 | | |
| TSS (mg/L) | 21980 | | | | 1757 |
| Total COD (mg/L) | 24700 | 27025 | | 24160 | 23700 |
| fCOD (mg/L) | 4040 | | | | |
| Total alkalinity ($CaCO_3$) (mg/L) | 9500 | 7000 | | 6900 | 11150 |
| TOC (mg/L) | 2040 | 2020 | 2100 | 2870 | 2390 |
| TIC (mg/L) | 1590 | 1810 | 1880 | 1740 | 1820 |

| Parameter | Sample 6 | Sample 7 | Sample 8 | Sample 9 | Sample 10 |
|---|---|---|---|---|---|
| Calcium (mg/L) | 1470 | 1550 | 1360 | 1240 | |
| Magnesium (mg/L) | 574 | 521 | 559 | 486 | |
| Sodium (mg/L) | 872 | 826 | 744 | 767 | |
| Potassium (mg/L) | 2570 | 2880 | 2480 | 2430 | |
| Aluminum (mg/L) | 107 | 103 | 95.4 | 104 | |
| Barium (mg/L) | 1.45 | 1.32 | 1.33 | 1.26 | |
| Strontium (mg/L) | 4.96 | 4.49 | 4.5 | 4.56 | |
| $NH_4$-N (mg/L) | 1180 | 1145 | 1136 | 1062 | |
| Copper (mg/L) | 45.1 | 39.5 | 39.4 | 39.8 | |
| Zinc (mg/L) | 48.5 | 39.6 | 41 | 40.9 | |
| Phosphate-P (mg/L) | 1160 | 1180 | 1120 | 936 | |
| TKN (mg/L) | 2620 | 2960 | 2750 | 2460 | |
| pH (units) | 7.61 | 7.83 | 7.69 | 7.64 | 7.59 |
| Iron (mg/L) | 86.5 | 72.3 | 73.8 | 60.2 | |
| Manganese (mg/L) | 45.8 | 45.4 | 49.4 | 47 | |
| Silicon (mg/L) | 118 | 106 | 79.2 | 78.9 | |
| Total Solids (mg/L) | 26625 | 32725 | 36475 | 30675 | |
| TDS (mg/L) | 11000 | 11700 | 11550 | 9960 | 9500 |
| TSS (mg/L) | 15625 | 21025 | 24925 | 20775 | |
| Total COD (mg/L) | 27300 | 27500 | 22868 | 30438 | |
| fCOD (mg/L) | 5580 | | 5434 | 5541 | 5153 |
| Total alkalinity ($CaCO_3$) (mg/L) | 12350 | 11800 | 10520 | 11200 | |

TABLE 1-continued

Parameters after Digestion

| | | | | |
|---|---|---|---|---|
| TOC (mg/L) | 3690 | 3290 | 2830 | 2560 |
| TIC (mg/L) | 1850 | 1750 | 1970 | 1870 |

TABLE 2

Parameters of Filtrate after Microfiltration Separation

| Parameter | Sample 1 | Sample 2 | Sample 3 | Sample 4 |
|---|---|---|---|---|
| Calcium (mg/L) | 7.7 | 10.9 | 10.6 | 16.3 |
| Magnesium (mg/L) | 3.7 | 3.6 | 4.3 | 5.3 |
| Sodium (mg/L) | 490 | 554 | 621 | 59 |
| Potassium (mg/L) | 1030 | 1760 | 1870 | 2060 |
| Aluminum (mg/L) | 0.78 | 1.25 | 0.67 | 0.442 |
| Barium (mg/L) | 0.01 | 0.004 | 0.002 | 0.003 |
| Strontium (mg/L) | 0.014 | 0.02 | 0.01 | 17.4 |
| $NH_4$ (mg/L) | 650 | 951 | 981 | 1054 |
| Copper (mg/L) | 0.05 | 0.07 | 0.06 | 0.067 |
| Zinc (mg/L) | 0.07 | 0.11 | 0.06 | 0.15 |
| Sulfate (mg/L) | 175 | 289 | 172 | 300 |
| Sulfide (mg/L) | <0.5 | | | |
| Chloride (mg/L) | 469 | 678 | 687 | 789 |
| Phosphate-P (mg/L) | 17.4 | 21 | 19.9 | 18.2 |
| Nitrate (mg/L) | 0.06 | 2.4 | 0.62 | 0 |
| Fluoride (mg/L) | 0.41 | 0.29 | 0.28 | 0.36 |
| Bromide (mg/L) | 0.05 | 1 | 0.05 | |
| TKN (mg/L) | 754 | | 960 | |
| pH (units) | 10 | 10.11 | 10.11 | 10 |
| Iron (mg/L) | 6.74 | 4.74 | 2.14 | 8.65 |
| Manganese (mg/L) | | 0.25 | 0.33 | 5.3 |
| Silicon (mg/L) | 11.3 | 12 | 17 | 16.8 |
| Total Solids (mg/L) | | | | |
| TDS (mg/L) | 4390 | 6330 | 6660 | 7450 |
| Total COD (mg/L) | 1430 | 2990 | 2750 | 2990 |
| Soluble COD (mg/L) | 1430 | 2990 | 2750 | |
| Total alkalinity ($CaCO_3$) (mg/L) | 2720 | 4710 | 5210 | 5620 |
| P alkalinity ($CaCO_3$) (mg/L) | 2100 | 600 | 600 | |
| TOC (mg/L) | 538 | 1040 | 865 | 1100 |
| TIC (mg/L) | 382 | 481 | 480 | 628 |
| Conductivity (mS/cm) | 6.54 | 8.98 | 9.14 | 10.3 |

| Parameter | Sample 5 | Sample 6 | Sample 8 |
|---|---|---|---|
| Calcium (mg/L) | 32.7 | 13/6 | 15.9 |
| Magnesium (mg/L) | 5.13 | 3.77 | 4.25 |
| Sodium (mg/L) | 603 | 634 | 617 |
| Potassium (mg/L) | 1760 | 1940 | 1990 |
| Aluminum (mg/L) | 1.98 | 2.18 | 1.8 |
| Barium (mg/L) | 0.021 | 0.004 | 0.003 |
| Strontium (mg/L) | 0.056 | 0.0196 | 0.03 |
| $NH_4$ (mg/L) | 709 | 0.068 | 704 |
| Copper (mg/L) | 0.675 | 0.068 | 0.03 |
| Zinc (mg/L) | 0.633 | 0.167 | 0.11 |
| Sulfate (mg/L) | 352 | 432 | 709 |
| Sulfide (mg/L) | 0.5 | 13.8 | |
| Chloride (mg/L) | 721 | 733 | 628 |
| Phosphate-P (mg/L) | 21 | 19 | 16.8 |
| Nitrate (mg/L) | 0.11 | 0.1 | 0.29 |
| Fluoride (mg/L) | 0.13 | | 0.17 |
| Bromide (mg/L) | 1 | 0.5 | 0.5 |
| TKN (mg/L) | | | |
| pH (units) | 10 | 10 | 10 |
| Iron (mg/L) | 11.3 | 6.04 | 20.3 |
| Manganese (mg/L) | 0.505 | 0.313 | 0.28 |
| Silicon (mg/L) | 13.2 | 8.09 | 6.95 |
| Total Solids (mg/L) | | | |
| TDS (mg/L) | 6910 | 7040 | 6580 |
| Total COD (mg/L) | 3120 | | |
| Soluble COD (mg/L) | 3120 | 3590 | 3300 |
| Total alkalinity ($CaCO_3$) (mg/L) | 4840 | 5240 | 3900 |
| P alkalinity ($CaCO_3$) (mg/L) | | | |

TABLE 2-continued

| Parameters of Filtrate after Microfiltration Separation | | | |
|---|---|---|---|
| TOC (mg/L) | 964 | 1100 | 1020 |
| TIC (mg/L) | 538 | 517 | 612 |
| Conductivity (mS/cm) | 9.32 | 10.3 | 10.26 |

The separation removed suspended solids. Only about 50% of dissolved solids were removed by the separation. Certain salts were removed, such as calcium and magnesium. Other salts remained in the filtrate, such as sodium and potassium. About 30% of ammonia was removed. However, the filtrate still contained high concentrations of ammonia. Accordingly, further treatment is needed for water recovery.

Samples 9 and 10 were each split into several samples. Parameters were measured after dosing with the separation additive and centrifugation. The measured values are show in Tables 3-4.

Accordingly, as shown by the data presented in Table 3, the addition of calcium hydroxide significantly increases pH of the wastewater. The addition of both calcium hydroxide and Alumafloc increases separation of total solids, decreases conductivity, and increases separation of soluble calcium.

As shown by the data presented in Table 4, there is no noticeable distinction between using a returned dosing agent and fresh.

However, the total solids content of the wastewater is still high. Additional treatment is necessary to recover water for dilution. After further treatment, it is expected that the ammonia-depleted filtrate will have about 8,350 ppm TDS, the organic-depleted filtrate will have about 4,300 ppm TDS, the return permeate will have about 250 ppm TDS, and the second return permeate will have about 800 ppm TDS. Combining effective amounts of the return permeate and the second return permeate will produce an acceptable dilution water.

TABLE 3

Parameters of Sample 9 after Dosing and Centrifugation

| | C1 | C2 | 9A | 9B | 9C | 9D | 9E |
|---|---|---|---|---|---|---|---|
| Softening | | | | | | | |
| Calcium hydroxide (g/L) | 0 | 0 | 4 | 5 | 8 | 9 | 10 |
| Stir time (min) | | | 120 | 120 | 120 | 120 | 120 |
| pH (units) | 7.68 | 7.68 | 8.69 | 9.22 | 9.39 | 9.48 | 9.62 |
| Total Solids (mg/L) | 32525 | 32525 | 33700 | 34000 | 36700 | 38025 | 39575 |
| Total COD (mg/L) | 24443 | 24443 | 27302 | 27975 | 19564 | 25927 | 24556 |
| Coagulation/flocculation | | | | | | | |
| Alumafloc (mg/L) | 10 | 0 | 10 | 10 | 10 | 10 | 10 |
| Stir time (min) | 30 | 30 | 2 | 2 | 30 | 30 | 30 |
| pH (units) | 7.92 | 7.90 | | | 9.37 | 9.46 | 9.59 |
| Centrifugation (wastewater) | | | | | | | |
| pH (units) | 7.94 | 7.93 | 9.03 | 9.24 | 9.37 | 9.48 | 9.62 |
| Total solids (mg/L) | 17925 | 17850 | 14100 | 13850 | 15950 | 15125 | 151250 |
| Conductivity (mS/cm) | 15.45 | 15.54 | 12.81 | 11.80 | 11.08 | 10.58 | 10.03 |
| Total COD (mg/L) | 14859 | 14784 | 13273 | 12947 | 13941 | 13952 | 13506 |
| Soluble COD (mg/L) | 4999 | 5491 | 4632 | 4741 | 5638 | 5365 | 5698 |
| Soluble calcium (mg/L) | 318 | 317 | 78.2 | 37.8 | 54.4 | 49.6 | 46.6 |

TABLE 4

Parameters of Sample 10 after Dosing and Centrifugation

| | C1 | 10A | 10B | 10C | 10D | 10E |
|---|---|---|---|---|---|---|
| Dosing | | | | | | |
| Ferric Sulfate (g/L) | 0.4 | 0.4 | 0.4 | 0.4 | 0.4 | 0.4 |
| Calcium hydroxide (g/L) | 4 | 4 | 4 | 5 | 5 | 5 |
| Calcium hydroxide source | return | return | fresh | return | return | fresh |
| Stir time (min) | 120 | 90 | 90 | 90 | 90 | 90 |
| pH (units) | 8.68 | 8.82 | 8.39 | 8.61 | 8.93 | 8.49 |
| Total Solids (mg/L) | 34400 | 34125 | 34625 | 34875 | 34425 | 35400 |
| Total COD (mg/L) | 26150 | 27902 | 32649 | 28610 | 25368 | 27561 |
| Alumafloc (mg/L) | 0 | 10 | 10 | 10 | 0 | 10 |
| ChemTreat P8175E (mg/L) | 0 | 0 | 0 | 0 | 10 | 0 |
| Centrifugation (wastewater) | | | | | | |
| pH (units) | 8.81 | 8.75 | 8.38 | 8.57 | 8.90 | 8.50 |
| Total solids (mg/L) | 14275 | 14325 | 13800 | 14400 | 14425 | 13295 |
| Conductivity (mS/cm) | 14.07 | 13.46 | 13.84 | 14.04 | 13.42 | 13.73 |
| Alkalinity total (mg/L $CaCO_3$) | 7000 | 6400 | 6700 | 6600 | 6600 | 6900 |
| Total COD (mg/L) | 12742 | 11402 | 9856 | 11610 | 12446 | 10596 |
| Soluble COD (mg/L) | 4632 | 4534 | 4307 | 4326 | 4503 | 3987 |
| Soluble calcium (mg/L) | 163.4 | 59.2 | 305.6 | 75.6 | 81.0 | 250.8 |

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Having thus described several aspects of at least one embodiment, it is to be appreciated various alterations, modifications, and improvements will readily occur to those skilled in the art. Any feature described in any embodiment may be included in or substituted for any feature of any other embodiment. Such alterations, modifications, and improvements are intended to be part of this disclosure and are intended to be within the scope of the invention. Accordingly, the foregoing description and drawings are by way of example only.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed.

What is claimed is:

1. A method of treating animal organic material comprising solids, the method comprising:
   diluting the animal organic material to produce an organic material slurry;
   anaerobically digesting the organic material slurry to produce a biogas and a digestate comprising ammonia;
   separating the digestate to produce a digestate solids and a filtrate having less than 1 ppm total suspended solids (TSS);
   removing ammonia from the filtrate to produce an ammonia-depleted filtrate;
   removing organic contaminants and divalent anions from the ammonia-depleted filtrate to produce an organic containing reject comprising divalent anions and an organic-depleted filtrate;
   concentrating the organic-depleted filtrate to produce a concentrated retentate and a return permeate;
   combining the digestate solids, the organic containing reject, and the concentrated retentate to produce a solids product; and
   directing the return permeate to dilute the animal organic material.

2. The method of claim 1, wherein the return permeate has 200-500 ppm total dissolved solids (TDS).

3. The method of claim 2, wherein the organic material slurry has 1,000 ppm-2,000 ppm ammonia, 1,800 ppm-2,500 ppm potassium, and 1,000-1,200 ppm sulfur.

4. The method of claim 1, further comprising dosing the digestate with at least one of a coagulant and a flocculant to produce a digestate sludge, separating the digestate sludge from the digestate, and combining the digestate sludge with the solids product.

5. The method of claim 4, further comprising controlling pH of the filtrate to be between about 9-10.

6. The method of claim 5, further comprising controlling pH of the ammonia-depleted filtrate to be between about 7-9 and dosing the ammonia-depleted filtrate with an antiscalant.

7. The method of claim 1, wherein the ammonia-depleted filtrate has 10 ppm ammonia or less.

8. The method of claim 1, wherein the organic-depleted filtrate has 10 ppm calcium or less and 10 ppm magnesium or less.

9. The method of claim 1, further comprising, separating organic contaminants and divalent anions from the organic containing reject to concentrate the organic containing reject and produce a second organic-depleted filtrate.

10. The method of claim 9, further comprising combining the second organic-depleted filtrate with the concentrated retentate to produce a dilute retentate;
    concentrating the dilute retentate to produce a second concentrated retentate and a second return permeate;
    directing the second return permeate to dilute the animal organic material; and
    combining the second concentrated retentate with the digestate solids and the organic containing reject.

11. The method of claim 1, further comprising processing the biogas to produce natural gas.

12. The method of claim 11, further comprising using energy generated by the biogas to power at least one operation of the method.

13. The method of claim 1, comprising producing zero liquid discharge.

14. A system for treating an animal organic material comprising solids, comprising:
    a dilution tank having a first inlet fluidly connected to a source of the animal organic material, a second inlet, and an organic material slurry outlet;
    an anaerobic digester having an inlet fluidly connected to the organic material slurry outlet, a biogas outlet, and a digestate outlet;
    a first solids-liquid separation subsystem having an inlet fluidly connected to the digestate outlet, at least one digestate solids outlet, and a filtrate outlet, the first solids-liquid separation subsystem configured to produce a filtrate having less than 1 ppm total suspended solids (TSS);
    an ammonia-reducing column having an inlet fluidly connected to the filtrate outlet, a countercurrent source of an acid, and an ammonia-depleted filtrate outlet;
    a second solids-liquid separation subsystem having an inlet fluidly connected to the ammonia-depleted filtrate outlet, at least one retentate outlet, and at least one return permeate outlet, the second solids-liquid separation subsystem configured to produce a return permeate having 200-500 ppm total dissolved solids (TDS);
    a production water storage tank having an inlet fluidly connected to the at least one return permeate outlet and an outlet fluidly connected to the second inlet of the dilution tank; and a solids product holding tank having a first inlet fluidly connected to the at least one digestate solids outlet and a second inlet fluidly connected to the at least one retentate outlet.

15. The system of claim 14, wherein the first solids-liquid separation subsystem comprises a centrifuge having the inlet fluidly connected to the digestate outlet, a first digestate solids outlet, and a digestate wastewater outlet, and a microfiltration unit having an inlet fluidly connected to the digestate wastewater outlet, a second digestate solids outlet, and the filtrate outlet.

16. The system of claim 15, further comprising at least one of a source of a coagulant and a source of a flocculant positioned upstream from the centrifuge.

17. The system of claim 16, wherein the coagulant and the flocculant are acceptable to produce a certified class A biosolids product.

18. The system of claim 16, further comprising a first source of a pH adjuster positioned upstream from the ammonia-reducing column.

19. The system of claim 18, further comprising a second source of a pH adjuster positioned upstream from the second solids-liquid separation subsystem and/or a source of an antiscalant positioned upstream from the second solids-liquid separation subsystem.

20. The system of claim 14, wherein the anaerobic digester is a continuous stirred tank reactor (CSTR).

21. The system of claim 14, wherein the second solids liquid separation subsystem comprises a nanofiltration unit having the inlet fluidly connected to the ammonia-depleted filtrate outlet, a first retentate outlet, and an organic-depleted filtrate outlet, and a reverse osmosis unit having an inlet fluidly connected to the organic-depleted filtrate outlet, a second retentate outlet, and a first return permeate outlet.

22. The system of claim 21, further comprising a second nanofiltration unit having an inlet fluidly connected to the first retentate outlet, a third retentate outlet fluidly connected to the solids product holding tank, and a second organic-depleted filtrate outlet.

23. The system of claim 22, further comprising a second reverse osmosis unit having an inlet fluidly connected to the second retentate outlet and the second organic-depleted filtrate outlet, a fourth retentate outlet fluidly connected to the solids product holding tank, and a second return permeate outlet fluidly connected to the production water storage tank.

24. The system of claim 14, wherein the source of the animal organic material comprises at least one of poultry manure, cow manure, swine manure, goat manure, sheep manure, and horse manure.

25. The system of claim 14, further comprising a biogas processing unit fluidly connected to the biogas outlet.

26. The system of claim 14, wherein the system is configured to produce zero liquid discharge.

* * * * *